(12) United States Patent
Ruiz et al.

(10) Patent No.: US 10,295,537 B2
(45) Date of Patent: May 21, 2019

(54) BIORECOGNITION ELEMENTS FOR RAPID DETECTION OF BIOCONTAMINATION

(71) Applicant: The United States of America, as represented by the Secretary of the Air Force, Washington, DC (US)

(72) Inventors: Oscar N Ruiz, Bellbrook, OH (US); Oksana Pavlyuk, Dayton, OH (US)

(73) Assignee: The United States of America as represened by the Secretary of the Air Force, Washington, DC (US)

( * ) Notice: Subject to any disclaimer, the term of this patent is extended or adjusted under 35 U.S.C. 154(b) by 0 days.

(21) Appl. No.: 15/889,621

(22) Filed: Feb. 6, 2018

(65) Prior Publication Data
US 2018/0224449 A1 Aug. 9, 2018

Related U.S. Application Data
(60) Provisional application No. 62/455,000, filed on Feb. 6, 2017.

(51) Int. Cl.
| | |
|---|---|
| *C07K 7/06* | (2006.01) |
| *G01N 33/28* | (2006.01) |
| *G01N 33/569* | (2006.01) |
| *G01N 33/68* | (2006.01) |
| *G01N 33/22* | (2006.01) |
| *G01N 33/58* | (2006.01) |
| *C07K 17/14* | (2006.01) |
| *C07K 19/00* | (2006.01) |
| *C07K 14/21* | (2006.01) |

(52) U.S. Cl.
CPC .......... *G01N 33/56911* (2013.01); *C07K 7/06* (2013.01); *C07K 14/21* (2013.01); *C07K 17/14* (2013.01); *C07K 19/00* (2013.01); *G01N 33/22* (2013.01); *G01N 33/2835* (2013.01); *G01N 33/56961* (2013.01); *G01N 33/582* (2013.01); *G01N 33/68* (2013.01); *G01N 2333/195* (2013.01)

(58) Field of Classification Search
CPC .................. C07K 7/06; G01N 33/2835; G01N 33/56911–56944; G01N 33/58; G01N 33/582; G01N 33/585; G01N 33/587; G01N 33/68
See application file for complete search history.

(56) References Cited

U.S. PATENT DOCUMENTS

| | | | | |
|---|---|---|---|---|
| 5,369,011 A * | 11/1994 | Ebersole | ................... | C12Q 1/24 210/290 |
| 6,747,137 B1 * | 6/2004 | Weinstock | ........... | C12Q 1/6895 435/6.13 |
| 2003/0233675 A1 * | 12/2003 | Cao | ....................... | C07K 14/195 800/279 |
| 2007/0020281 A1 * | 1/2007 | Kearney | ............. | C07K 16/1278 424/164.1 |
| 2007/0281302 A1 * | 12/2007 | Turnbough, Jr. | ........ | C07K 7/06 435/6.15 |
| 2009/0300802 A1 * | 12/2009 | Ryan | ..................... | C07K 14/415 800/298 |
| 2011/0214205 A1 * | 9/2011 | Dietrich | ............... | C07K 14/415 800/281 |
| 2012/0156134 A1 * | 6/2012 | Squires | ................ | A61K 51/088 424/9.1 |
| 2014/0352202 A1 | 12/2014 | Ruiz | | |
| 2017/0260467 A1 | 9/2017 | Ruiz | | |

FOREIGN PATENT DOCUMENTS

WO WO-2016138245 A2 * 9/2016 ....... G01N 33/57419

OTHER PUBLICATIONS

Database UniProt [online], submitted Mar. 2013. Harkins et al. ID N1WG03_9LEPT, retrieved Nov. 15, 2018.*
Database UniProt [online], submitted May 2014. F. Horn. ID A0A060ZTP8_9ACTN, retrieved Nov. 15, 2018.*
Database UniProt [online], submitted Mar. 2016. O. Ploux. ID A0A142FLZ9_9ALTE, retrieved Oct. 2, 2018.*
Database UniProt [online], submitted Nov. 2013. Young et al, "Opisthorchis viverrini—life in the bile duct". ID A0A074Z8C1_9TREM, retrieved Nov. 15, 2018.*
Database UniProt [online], submitted Jun. 2016. Kjaerup et al. ID A0A1C5DCY8_9ACTIN, retrieved Nov. 15, 2018.*
Database Uniprot [online], submitted Apr. 2016. Helminth Genome Consortium. ID A0A158QS45_9CEST, retrieved Oct. 30, 2018.*
Database UniProt [online]. 2013, Swart et al, "The Oxytricha trifallax Macronuclear Genome: A Complex Eukaryotic Genome with 16,000 Tiny Chromosomes". PLoS Biol. 11:E1001473-E1001473. ID J9IUQ2_9SPIT, retrieved Nov. 15, 2018.*
E. G. Rawling et al., "Epitope mapping of the Pseudomonas aeruginosa major outer membrane porin protein OprF," Infection and Immunity, vol. 63 (1995) 38-42.

(Continued)

*Primary Examiner* — Jeffrey E. Russel
(74) *Attorney, Agent, or Firm* — AFMCLC/JAZ; Chastity Whitaker

(57) ABSTRACT

A biorecognition element for detection of fuel biocontamination. The biorecognition element includes a sequence selected from SEQ. ID No. 10, SEQ. ID No. 13, SEQ. ID No. 22, SEQ. ID No. 27, SEQ. ID No. 31, SEQ. ID No.40, SEQ. ID No.67, SEQ. ID No. 68, SEQ. ID No. 69, SEQ. ID No. 70, SEQ. ID No. 71, and SEQ. ID No.72, an amine-functionalized quantum dot, a C-terminal, three-glycine plus cysteine linker, and a reporter molecule conjugated to the amine-functionalized quantum dot. Biocontaminants are labeled by the biorecognition element and observed via the reporter molecule of the biorecognition element.

13 Claims, 14 Drawing Sheets
(1 of 14 Drawing Sheet(s) Filed in Color)
Specification includes a Sequence Listing.

(56) References Cited

OTHER PUBLICATIONS

E. Sugawara et al., "Alterantive folding pathways of the major porin OprF of Pseudomonas aeruginosa," FEBS J., vol. 279 (2012) 910-918.

I. Chen et al., "Phage display evolution of a peptide substrate for yeast biotin ligase and application to two-color quantum dot labeling of cell surface proteins," JACS, vol. 129 (2007) 6619-6625.

R. Edgar et al., "High-sensitivity bacterial detection using biotin-tagged phage and quantum-dot nanocomplexes," PNAS, vol. 103 (2006) 4841-4845.

J. X. Huang et al., "Development of anti-infectives using phage display: biological agents against bacteria, viruses, and parasites," Antimicrob. Agents Chemother., vol. 56 (2012) 4569-4582.

M. A. Walling et al., "Quantum dots for live cell and in vivo imaging," Ing. J. Mol. Sci., vol. 10 (2009) 441-491.

T. S. Gunasekera et al., "Transcriptional profiling suggests that multiple metabolic adaptations are required for effective proliferation of Pseudomonas aeruginosa in jet fuel," Environ. Sci. & Tech., vol. 47 (2013) 13449-13458.

R. C. Striebich et al., "Characterization of the F-76 diesel and Jet-A aviation fuel hydrocarbon degradation profiles of pseudomonas aeruginosa and Marinobacter hydrocarbonoclasticus," Int'l Biodegrad. & Biodeter., vol. 93 (2014) 33-43.

\* cited by examiner

*P. Aeruginosa – ATCC33988*

No Label

QD545

OBP12-QD545
(SEQ. ID No. 22)

OBP11-QD545
(SEQ. ID No. 27)

OPP1-QD545
(SEQ. ID No. 67)

LP-FITC

BIORECOGNITION ELEMENTS FOR RAPID DETECTION OF BIOCONTAMINATION

Pursuant to 37 C.F.R. § 1.78(a)(4), this application claims the benefit of and priority to prior filed Provisional Application Ser. No. 62/455,000, filed Feb. 6, 2017, which is expressly incorporated herein by reference.

RIGHTS OF THE GOVERNMENT

The invention described herein may be manufactured and used by or for the Government of the United States for all governmental purposes without the payment of any royalty.

FIELD OF THE INVENTION

The present invention relates generally to fuel contamination and, more particularly, to methods and devices for evaluating fuel contamination.

BACKGROUND OF THE INVENTION

Effective monitoring of microbial growth in fuel is of great importance in prolonging the usable lifetime of vehicle and fuel systems and to ensure safety. Biocontamination may cause significant damage to a fuel system including, hydrocarbon degradation, changes in fuel properties and quality, corrosion, filter clogging, deactivation of fuel-water coalescers, coating degradation, inaccurate fuel level readings, decreased vehicle performance, and is often detected after the fuel system is compromised. Early detection of biofouling enables the use of cost-effective mitigation strategies that may reduce the contamination's impact on the fuel system. Thus, an early warning detection sensor to alert maintenance crew of biocontamination could save millions of dollars per year in repair costs over the lifetime of the vehicle and fuel system.

Conventionally, there has been no simple and reliable method for detecting microbes and biodeterioration in fuel. The methods used today are typically performed by highly trained scientists in laboratories. These laboratories are likely equipped with molecular-based instrumentation (such as PCR and sequencing instruments) that are quantitative in nature and do not differentiate between living and non-living microbes. Colony counting methods are quantitative and do not require expensive instrumentation; however, colony counting is very time consuming and only capable of detecting culturable bacteria, which may represent just 10% of all bacteria present within a fuel system.

Commercially-available kits are available, but are also cumbersome, inaccurate, and, at best, semi-quantitative. Some of these kits require multi-date culture growth for visual analysis or quantification of Adenosine Triphosphate ("ATP"). However, ATP levels are highly dependent on the growth stage of the microbe.

Other commercially-available kits use antibody-based detection methods. Antibodies are affected by degradation and are negatively influenced by the presence of fuel.

In view of the foregoing, a simplified, accurate method of detection biocontamination in a short timeframe would be greatly useful in preserving fuel systems and minimizing repair and replacement costs due to biodeterioration.

SUMMARY OF TIE INVENTION

The present invention overcomes the foregoing problems and other shortcomings, drawbacks, and challenges of how to quickly, reliably, and accurately detect biocontamination within fuel systems. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a biorecognition element for rapid detection of biocontamination includes SEQ. ID No. 10, SEQ. ID No. 13, SEQ. ID No. 22, SEQ. ID No. 27, SEQ. ID No. 31, SEQ. ID No.40, SEQ. ID No.67, SEQ. ID No. 68, SEQ. ID No. 69, SEQ. ID No. 70, SEQ. ID No. 71, or SEQ. ID No.72.

According to various aspects of the present invention, the biorecognition element may include one or more of a C-terminal, three-glycine plus cysteine linker cross-linking the biorecognition element to a quantum dot, an amine-functionalized quantum dot, and a reporter molecule. The reporter molecule may be fluorescent molecule, a chemiluminescent molecule, a colorimetric molecule, or a signal transducing nanomaterial.

Other embodiments of the present invention include a method of detecting biocontamination and include acquiring a sample and isolating microbes therefrom. The microbes are labeled with a first reporter conjugated to a biorecognition element. The biorecognition element is selected from the group consisting of SEQ. II) No. 10, SEQ. ID No. 13, SEQ. ID No. 22, SEQ. ID No. 27, SEQ. ID No. 31, SEQ. ID No.40, SEQ. ID No.67, SEQ. ID No. 68, SEQ. ID No. 69, SEQ. ID No. 70, SEQ. ID No. 71, and SEQ. ID No.72.

According to some aspects of the present invention, isolating microbes from the fuel sample may include moving microbes from a fuel phase to an aqueous phase, drawing the aqueous phase from the fuel phase, and obtaining a microbe pellet from the aqueous phase by centrifugation. According to other aspects, isolating the microbes may include filtration.

Yet other embodiments of the present invention include a biocontamination assay kit. The kit includes a biorecognition element that is element selected from the group consisting of: SEQ. ID No. 10, SEQ. ID No. 13, SEQ. ID No. 22, SEQ. ID No. 27, SEQ. ID No. 31, SEQ. ID No.40, SEQ. ID No.67, SEQ. ID No. 68, SEQ. ID No. 69, SEQ. ID No. 70, SEQ. ID No. 71, and SEQ. ID No.72. A C-terminal, three-glycine plus cysteine linker is on the biorecognition element. An amine-functionalized quantum dot is cross-linked to the cysteine linker, and a reporter molecule that is conjugated to the amine-functionalized quantum dot.

In some aspect of the present invention, the reporter molecule may be a fluorescent molecule, a chemiluminescent molecule, a colorimetric molecule, or a signal transducing nanomaterial.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments of the present invention and, together with a general description of the invention given above, and the detailed description of the embodiments given below, serve to explain the principles of the present invention.

FIGS. 5-10 are exemplary fluorescent images and fluorometry of fuel-degrading bacterial labeled with OprF and Opr86 BREs conjugated to QD545.

DETAILED DESCRIPTION OF THE INVENTION

Figure 1:
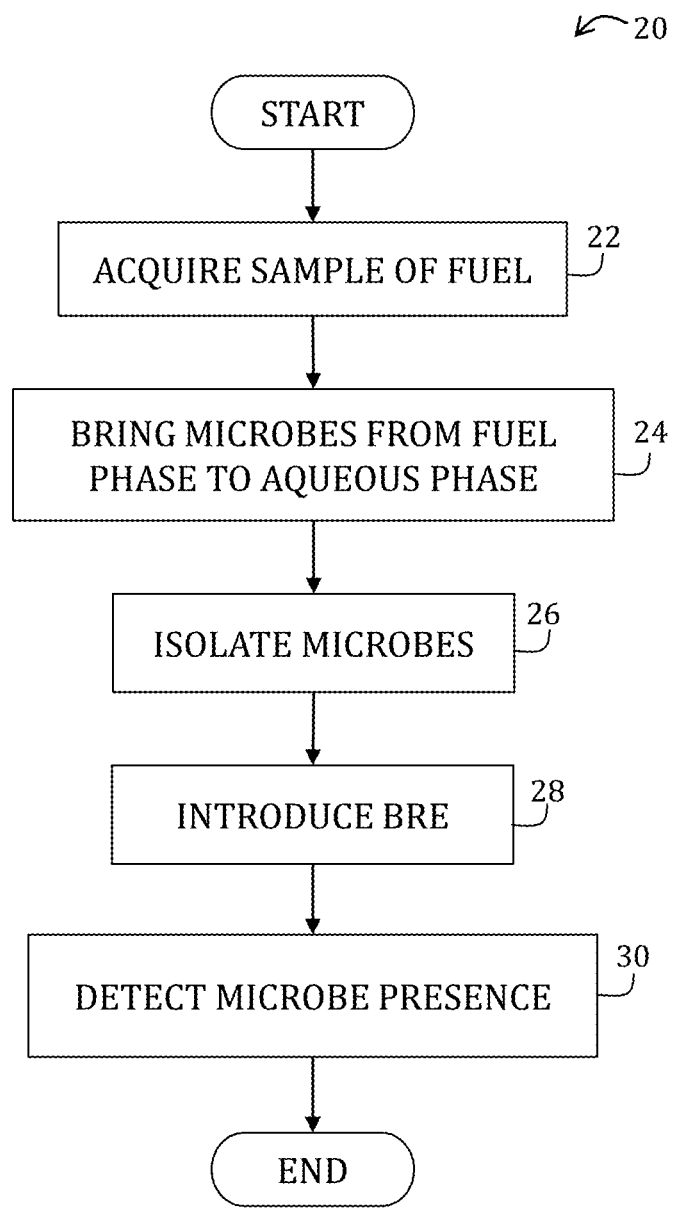
FIG. 1 is a flow chart illustrating a method of detecting fuel contamination according to one embodiment of the present invention is shown.

Several species of bacteria are known to contaminate fuel, such as prokaryotes, Gram negative bacteria, and, the notoriously difficult to eradicate, *Pseudomonas*. Persistence of *P. aeruginosa* and other *Pseudomonas* species in the harshest environments is believed to be due in part to low permeability of outer membrane proteins (i.e., porins) and the presence of efflux transporter proteins (i.e., efflux pumps) that extrude xenobiotics. Together, these proteins enable *Pseudomonas* to proliferate in the harsh environments that include antimicrobial drugs, hydrocarbons, and fuel.

One such transporter protein, OprF, is a major porin of *P. aeruginosa*. OprF is responsible for outer membrane permeability, non-specific diffusion of small polar nutrients across the cellular membrane and has also been implicated in other important physiological functions. OprF serves as a connector between outer and inner cellular membranes such that deletion of OprF produces an unstable outer membrane and aberrant cell morphology. The 326 aa-long OprF includes 15 transmembrane motifs comprising the β-barrel and eight highly conserved extracellular loops that have been used as linear epitopes for the development of *P. aeruginosa* specific antibodies. This secondary structure of OprF regulates membrane permeability by adopting an open conformation or a closed conformation, depending on the cell requirements.

OprF is also thought to be a modulator of quorum sensing, enhanced bacterial virulence, and expression of OprF is required for the formation of anaerobic biofilms. OprF has been shown to uptake aromatic solvents, including toluene, and is regulated at the transcriptional level by the presence of hydrocarbons.

A similarly, outer membrane protein, Opr86, is highly conserved in Gram negative bacteria and is essential in outer membrane biogenesis. Opr86 is responsible for the assembly and insertion of β-barrel outer membrane proteins via complex formation with other lipoproteins.

Antibodies against Opr86 have prevented biofilm formation by *P. aeruginosa* PAO1. Organic solvents and fuel were shown to up-regulate the expression of Opr86.

The amino acid composition and structure of *P. aeruginosa* Opr86 and OprF are known; however, developing peptides that can detect the multiplicity of fuel degrading microorganisms that may be present in the fuel system and retain the binding activity in the presence of fuel has been a challenge in the past.

Biorecognition elements ("BREs") are short, nucleic acid-based aptamers or peptides configured to mimic antibody-antigen interactions, and may be obtained by high through-put screening methods, such as systematic evolution of ligands by exponential enrichment ("SELEX") and phage display. Small, seven-to-12 amino acid ("aa") peptides are ideal BREs and provide several benefits over other molecular probes, such as high chemical diversity, ease of synthesis and conjugation to the surface of a signal transducer, and high stability in harsh environments, such as fuel.

Peptide BREs are similar to antibody-antigen binding in that both have high affinity and specificity; however, unlike antibodies, short peptides do not require immunogenic antigens, post-translational modifications (such as disulfide bonds), and are not prone to batch variation. Moreover, peptide BREs are not prone to denaturation, have a longer shelf life, and are potentially reusable, all of which are unlike conventional large, multi-domain proteins and antibodies. Shorter, single-domain antibodies, also known as nanobodies, have even been shown to retain antigen binding activity in the presence of jet fuel.

Using the conserved extracellular loop epitopes of OprF and Opr86 outer membrane proteins as antigens, binding BREs were isolated using phage display in the presence of fuel. While multiple extracellular loops of OprF were shown to be immunogenic, the epitope of sequence GTYETGNKVH (SEQ. ID No. 1) was shown to be most reactive for the production of monoclonal antibodies. This 11 aa-long sequence (an 55-56 of OprF) exhibits a great level of conservation across different *Pseudomas* species and is hereinafter referred to as "OprF1."

With the foregoing, and turning now to FIG. 1, a method 20 of detecting fuel contamination is shown. At start, a sample of fuel for testing is acquired (Block 22). The sample may include a fuel phase, an aqueous phase, or both and may be acquired from fuel dispensers, fuel tanks, pipelines, and so forth. The fuel may be any liquid type fuel, such as jet fuel, diesel, biodiesel, kerosene, gasoline with or without alcohol content (such as biofuels), and so forth; however, embodiments of the present invention may also be suitable for detecting microbial contamination in hydraulic fluids, lubricants, synthetic and natural oils, hydrocarbon-based plastics, fatty acid methyl esters, and so forth. The sample size may vary, but should be sufficient large to capture the biodiversity within the fuel sample—for example, 0.5 L to 1 L may be sufficient in some instances.

The fuel sample may then be prepared for collecting microbes contained therein. According to the illustrative embodiment of the present invention, phosphate-buffered saline ("PBS") buffer (pH 7.2) may be added to the sample to bring microbes in the fuel phase into the PBS buffer/aqueous phase (Block 24). The PBS buffer/aqueous phase may be transferred from the sample and centrifuged (such as at 10,000 RPMs) to yield a microbe pellet (Block 26). Alternatively, although not specifically shown, a filter may be used to separate and recover microbes from fuel samples to allow direct detection on the filter or to recover the microbes to a solution for detection as described above. A 0.1 μm to 0.22 μm diameter filter made of cellulose, polyvinylidene difluoride ("PVDF"), or other material, or a filter made of graphene oxide nanomaterial, may be used to filter an aliquot of fuel (i.e., fuel, water, or fuel and water) while retaining and separating microbes out of the fuel for direct detection onto the filter with BRE-QDs. Alternatively, microbes may be recovered from the filter into an aqueous solution by agitation or vortex for detection as described above.

With the microbes isolated, and using a biorecognition element selected, hereinafter referred to as "OBP" and "OPP" from SEQ. ID No. 10, SEQ. ID No. 13, SEQ. ID No. 22, SEQ. ID No. 27, SEQ. ID No. 31, SEQ. ID No.40, SEQ. ID No.67, SEQ. ID No. 68, SEQ. ID No. 69, SEQ. ID No. 70, SEQ. ID No. 71, and SEQ. ID No.72, microbes having Opr porin protein may be detected. In that regard, OBPs and OPPs may be conjugated to reporter such as a fluorescent, chemiluminescent, and colorimetric molecules or signal transducing nanomaterials for optical detection of the target without altering the antigen-binding capacity and biorecognition activity of the BRE. Thus, according to some embodiments of the present invention, OprF1 may be used as biofunctionalized quantum dot ("QD") reporter fluorophores. While other embodiments may utilize conventional chemical dyes, QDs may be used in lieu thereof to provide improved brightness and stability against photobleaching. QDs broad absorption spectra allow for utilization of a single excitation source; the narrow symmetrical emission spectra, size-dependent quantum yields, and large Stokes shifts make QDs excellent reporter fluorophores for multiplexed detection of different microorganisms.

The resulting BRE-QD conjugates may be used as labeling reagents in a lateral flow assay for the quantitative detection of Gram negative fuel-degrading bacteria in the presence of fuel. The assay specificity and limit of detection ("LOD") was determined and its application in the detection of bacteria in contaminated fuel samples from field tanks was demonstrated.

The BRE-QD conjugates may then be introduced to the microbes (Block 28). While the amount of BRE-QD introduced to the isolated microbe may vary, using the exemplary 0.5 L to 1 L fuel sample noted above, 0.1 mL of 1.5 μM Peptide BRE-QD solution in PBS at room temperature for 30 min may be used to label the microbes. If desired or necessary, the microbes may be washed and resuspended prior to detection.

Detection of the microbes depends on the labeling embodiment used (Block 30). For instance, using the BRE-QD embodiment, presence and amount of microbes may be detected measuring fluorescence (emission spectra) with a fluorometer. According to one specific embodiment, a Cary Eclipse Fluorimeter at 330 nm excitation and fluorescence collection at 545 nm or any other may be used.

According to other embodiments of the present invention, the OBP and OPP may be biofunctionalized with gamut fluorescent and chemiluminescent molecules (e.g., dyes and particles) with the peptide BREs for fluorescent and colorimetric microbial detection. The ordinarily-skilled artisan having the benefit of the disclosure made herein would readily appreciate how such biofunctionalized BREs may be detected and reported.

Moreover, OBP and OPP may be used to biofunctionalize optical transducers (such as antenna resonators or photonic gratings), electrical transducers (such as graphene-based field effect transistors, quartz crystal microbalance), graphene oxide-based sensing materials, and so forth to provide real-time detection of microbial contamination of fuel supplies and tanks.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

Biotinylated at its N-terminal, an OprF1 synthetic peptide was used for solution biopanning screening of a commercially-available M13 bacteriophage library displaying heptameric peptides at the N-terminal of P3 coat protein. Solution-phase biopanning provided the benefit of including the availability of all the OprF1 aa residues for interaction with the potential peptide binder with lessened likelihood of isolating unspecific peptides that might bind to the capture element used to purify the phage-antigen complex (i.e., magnetic or protein G beads).

Generally, solution-phase biopanning was carried out as described by the manufacturer (New England Biolabs, Ipswich, Mass.) with some modifications, including the changing of pH from 7.0 to 5.5 and 8.5 and adding 1% v/v of Jet A fuel. The first round of selection was carried out by diluting Ph.D.-7 bacteriophage library 100-fold in 0.1% Tris buffer saline plus Tween 20 (0.1% TBST) at the appropriate pH for selection plus fuel. Subsequently, the phage library was incubated with 1 μg of N-terminal biotinylated target protein fragment (OprF1: GTYETGNKKVH (SEQ. ID No. 1), OprF2: ADIKNLADFMK QYPSTSTT (SEQ. ID No. 2), Opr86: YGSTDGLPFYENYYAGGFNSVRGFKDSTLGPR STP (SEQ. ID No. 3)) for 1 hr at 25° C. Phage-protein complexes were captured with 50 μL of streptavidin magnetic microbeads, unbound phages were removed, and the pellet sample washed 10-times with 1 mL of 1× Tris buffer saline ("TBS") plus 0.05% TBST to remove weakly bound phage particles. Bound bacteriophages were eluted from the beads by lowering the pH (0.2 M Glycine-HCl, pH 2.2) while rotating gently for 10 min at 25° C. After neutralization with 1 M Tris-HCl, pH 9.1, eluted phages were amplified by infection of E. coli strain ER 2738 grown in Luria-Bertani ("LB") broth medium until early-log phase (OD600 0.1-0.5). Titer of the amplified phage (more than $10^{10}$ pfu/mL) was determined by infection into E. coli ER2738 and subsequent growth in selective medium containing X gal/IPTG. Amplified phages from round 1 were pre-cleared with streptavidin-coated magnetic microbeads (50 μL) to further remove non-specific binders and then used as the input phage for round 2 of selection. Enrichment of the bacteriophage pool was achieved by performing 4 rounds of selection under the appropriate pH plus jet fuel condition. Genomic DNA from individual clones was sequenced by GenScript (Piscataway, N.J.).

OprF1-phage complexes were captured with streptavidin coated magnetic microbeads; non-binding phages were removed by a series of washes with 0.1% Tween-TBS, pH 7.

OprF-binding phages were eluted by lowering pH to 2, neutralization with Glycine Buffer (pH 9), infection of the *E. coli* ER2738 host, and subsequent amplification. The amplified phage pool was isolated by precipitation with PEG/NaCl and titered to determine phage concentration.

Figure 2:
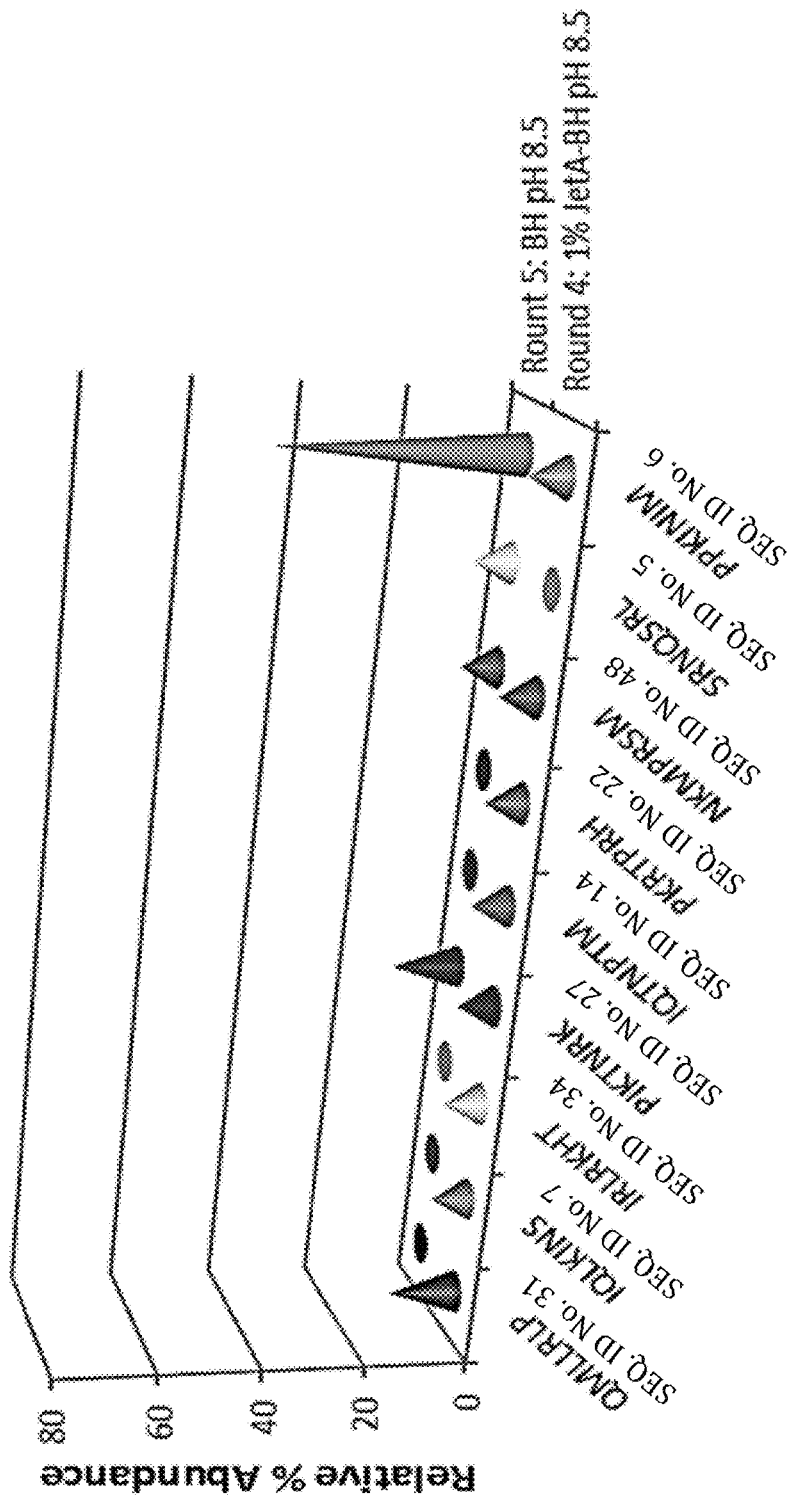
FIG. 2 is a graphical representation of OprF-binding peptide distribution as a function of fuel additive.
Figure 3:
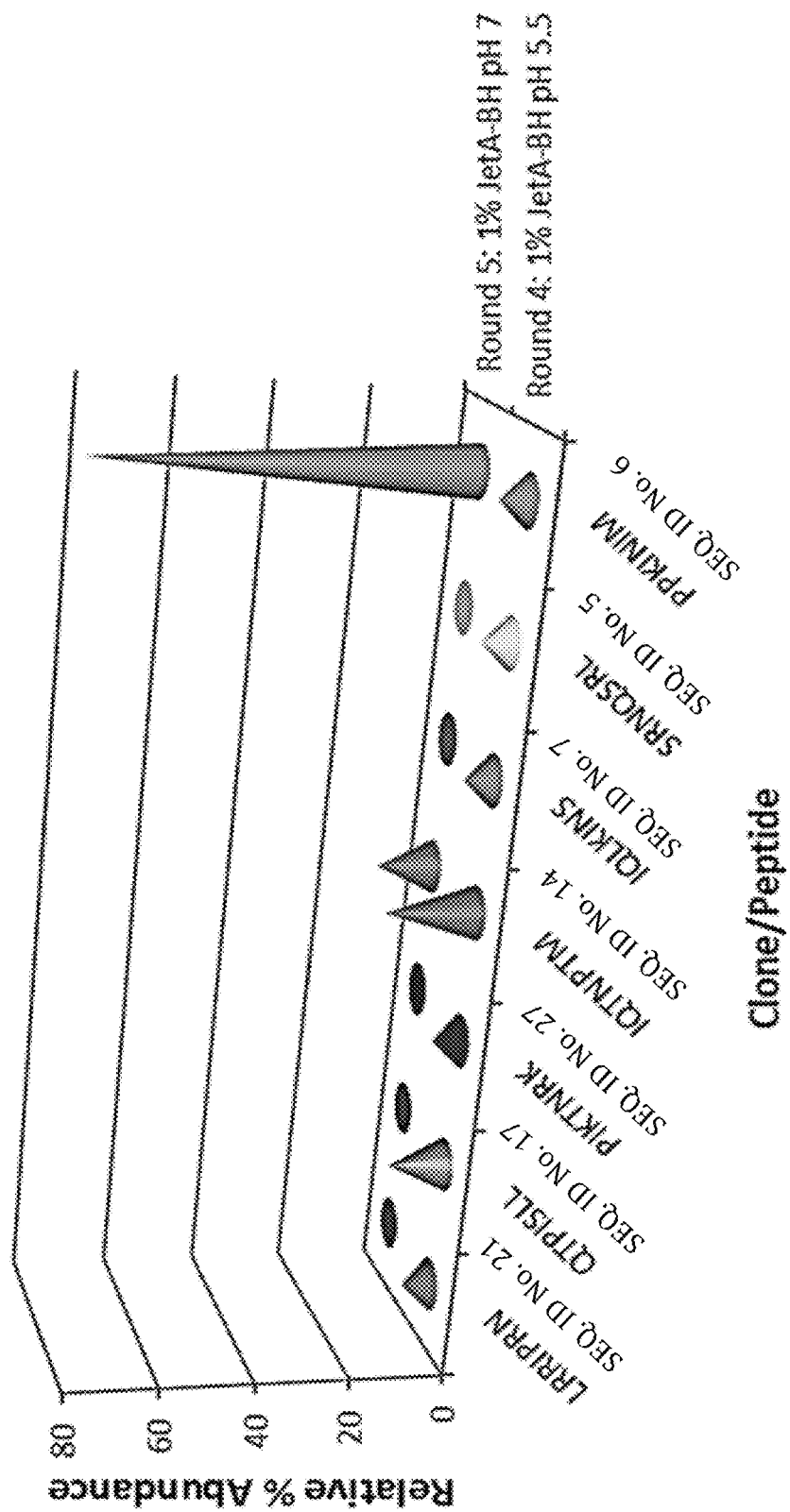
FIG. 3 is a graphical representation of OprF-binding peptide distribution as a function of pH.

Recombinant phage clones were selected using X-Gal/IPTG, which produced a blue color on phage infected *E. coli* colonies. After the amplification of multiple phage isolates carrying a single heptapeptide sequence (i.e., monoclonal phages), genomic DNA was isolated and sequenced to determine the aa sequences of the OprF-Binding Peptides ("OBPs"). Isolated monoclonal phages were sequenced after each round of selection. After four rounds of selection, the phage pool was enriched for OprF1-binding phages with three consensus sequences (see Table 1, below), and predominantly the PPKINIM (SEQ. ID No. 6) peptide with 80% abundance based on round 4 clones. Unfortunately, this type of binding profile is known to be characteristic of "library collapse," wherein the loss of library diversity is a result of enrichment for bacteriophages displaying peptides conferring advantageous growth properties to the phages independent of binding affinity to the target, such as a more efficient infectivity or phage assembly/extrusion from the bacterial host cell. Such library collapse was confirmed when the round 4 phage pool was used as an input phage for the next round of biopanning in non-physiological conditions: pH 8.5 and 1% v/v Jet-A fuel in Bushnell-Haas minimal media. These biopanning conditions were chosen to mimic the fuel tank milieu, where the fuel-degrading bacteria would ultimately be detected. Under these conditions, the binding of the selected library phage was abolished and only wild-type M13 was isolated after round 5. This observation indicated that selective pressure other than multiple rounds of biopanning and amplification must be applied to isolate OprF1-specific bacteriophages lacking growth advantages. To achieve this goal, Bushnell-Haas minimal media supplemented with 1% v/v Jet-A at non-physiological pH (pH 5.5 or pH 8.5) was used for all rounds of biopanning and removal of non-binding phages. Using these conditions, the profile of OprF-OBPs changed dramatically (see FIGS. 2 and 3), and many additional peptide binders were identified (Tables 2 and 3, below). The M13 bacteriophage was shown to survive in non-aqueous solvents and acidic/basic pHs that mimicked fuel tank conditions.

If no fuel additive was used (FIG. 2) or the pH at physiological pH of 7 (FIG. 3), the phage library converged back to the PPKINIM (SEQ. ID No. 6) peptide, obliterating the selection of phages displaying the OprF1-specific peptides and lacking advantageous growth properties.

Because library collapse is a direct consequence of amplification in *E. coli*, the step was omitted to yield a more accurate percentage of abundance that would be more reflective of the binding affinity of OprF peptides, shown in Table 4, below.

TABLE 1

| Round 3 Clone | aa Sequence | SEQ. ID No. | Round 4 Clone | aa Sequence | SEQ. ID No. |
|---|---|---|---|---|---|
| 1_OPRF1R3 | NRNIRIH | 4 | 2_OPRF1R4 | PPKINIM | 6 |
| 2_OPRF1R3 | SRNQSRL | 5 | 3_OPRF1R4 | PPKINIM | 6 |
| 3_OPRF1R3 | PPKINIM | 6 | 4_OPRF1R4 | RRSNSQL | 13 |
| 4_OPRF1R3 | NRNIRIH | 4 | 5_OPRF1R4 | PPKINIM | 6 |
| 5_OPRF1R3 | IQLKINS | 7 | 6_OPRF1R4 | PPKINIM | 6 |
| 6_OPRF1R3 | RTRRKSN | 8 | 7_OPRF1R4 | IQLKINS | 7 |
| 9_OPRF1R3 | ILKSITH | 9 | 8_OPRF1R4 | PPKINIM | 6 |
| 10_OPRF1R3 | NMTNPPP | 10 | 9_OPRF1R4 | PPKINIM | 6 |
| 12_OPRF1R3 | NTRTMIK | 11 | 10_OPRF1R4 | PPKINIM | 6 |
| 24_OPRF1R3 | IQLKINS | 7 | 11_OPRF1R4 | RRSNSQL | 13 |
| 25_OPRF1R3 | PPKINIM | 6 | 13_OPRF1R4 | PPKINIM | 6 |
| 26_OPRF1R3 | PPKINIM | 6 | 14_OPRF1R4 | PPKINIM | 6 |
| 27_OPRF1R3 | IKPTNRT | 12 | 15_OPRF1R4 | PPKINIM | 6 |
| 28_OPRF1R3 | PPKINIM | 6 | 16_OPRF1R4 | PPKINIM | 6 |
| 29_OPRF1R3 | PPKINIM | 6 | 17_OPRF1R4 | PPKINIM | 6 |

Fourteen monoclonal OprF1-binding phages were combined at equal concentrations in Bushnell-Haas, pH 8.5, supplemented with 1% v/v Jet-A and incubated with biotinylated OprF1, followed by alternative washes with Bushnell-Haas, pH 8.5 or pH 5.5, supplemented with Jet-A. Eluted unamplified phages were titered and 30 randomly selected clones were used to determine percent abundance and relative affinity for OprF. Using these conditions, the relative percent abundance of the PPKINIM (SEQ. ID No. 6) clone was determined to be 3%, which is in stark contrast to the 80% abundance under physiological conditions.

TABLE 2

| R3 Clone | Sequence | SEQ. ID No. | R4 Clone | Sequence | SEQ. ID No. | R5 Clone | Sequence | SEQ. ID No. | R6 Clone | Sequence | SEQ. ID No. |
|---|---|---|---|---|---|---|---|---|---|---|---|
| 5oprF1FAR3 | IQTNPTM | 14 | 21oprF1FAR4 | LRRIPRN | 21 | 1oprF1FAR5 | ** | — | 1oprF1FAR6 | NRNIRIH | 4 |
| 6oprF1FAR3 | NRNIRIH | 4 | 9oprF1FAR4 | PPKINIM | 6 | 2oprF1FAR5 | PPKINIM | 6 | 2oprF1FAR6 | PPKINIM | 6 |
| 7oprF1FAR3 | SLQHLRS | 15 | 11oprF1FAR4 | PKRRSQN | 23 | 3oprF1FAR5 | PPKINIM | 6 | 3oprF1FAR6 | PPKINIM | 6 |
| 8oprF1FAR3 | IQTNPTM | 14 | 13oprF1FAR4 | MLLMTPH | 24 | 4oprF1FAR5 | IQTNPTM | 14 | 4oprF1FAR6 | PPKINIM | 6 |
| 9oprF1FAR3 | RRSNSQL | 13 | 14oprF1FAR4 | PNRRSRS | 25 | 5oprF1FAR5 | PPKINIM | 6 | 5oprF1FAR6 | QMLLRLP | 31 |
| 25oprF1FAR3 | RPRISII | 16 | 15oprF1FAR4 | MTRRQSI | 26 | 6oprF1FAR5 | IKTSHPR | 30 | 6oprF1FAR6 | PPKINIM | 6 |
| 26oprF1FAR3 | QTPISLL | 17 | 18oprF1FAR4 | QTPISLL | 17 | 7oprF1FAR5 | PPKINIM | 6 | 7oprF1FAR6 | PPKINIM | 6 |
| 27oprF1FAR3 | KLNLMRT | 18 | 19oprF1FAR4 | PIKTNRK | 27 | 8oprF1FAR5 | PPKINIM | 6 | 8oprF1FAR6 | PPKINIM | 6 |
| 28oprF1FAR3 | MKLIIRM | 19 | 25oprF1FAR4 | QTPISLL | 17 | 9oprF1FAR5 | PPKINIM | 6 | 9oprF1FAR6 | PPKINIM | 6 |
| 29oprF1FAR3 | NRNIRIH | 4 | 26oprF1FAR4 | IQTNPTM | 14 | 10oprF1FAR5 | PPKINIM | 6 | 10oprF1FAR6 | PPKINIM | 6 |
| 30oprF1FAR3 | IQLKINS | 7 | 27oprF1FAR4 | IQLKINS | 7 | 11oprF1FAR5 | PPKINIM | 6 | 11oprF1FAR6 | PPKINIM | 6 |
| 31oprF1FAR3 | PRRNRPL | 30 | 28oprF1FAR4 | MPMMLMM | 28 | 12oprF1FAR5 | PPKINIM | 6 | 12oprF1FAR6 | KIIMLTR | 6 |
| 32oprF1FAR3 | NMTNPPP | 10 | 29oprF1FAR4 | SRNQSRL | 5 | 13oprF1FAR5 | PPKINIM | 6 | 13oprF1FAR6 | PPKINIM | 6 |
| 33oprF1FAR3 | IQTNPTM | 14 | 30oprF1FAR4 | IQTNPTM | 13 | 14oprF1FAR5 | IQTNPTM | 14 | 14oprF1FAR6 | PPKINIM | 6 |
| 34oprF1FAR3 | LRRIPRN | 21 | 31oprF1FAR4 | LLRMRHS | 29 | 15oprF1FAR5 | PPKINIM | 6 | 15oprF1FAR6 | PSQRMTM | 32 |
| 35oprF1FAR3 | PKRTPRH | 22 | 34oprF1FAR4 | IQTNPTM | 14 | 16oprF1FAR5 | PPKINIM | 6 | 16oprF1FAR6 | PPKINIM | 6 |

TABLE 3

| R3 Clone | Sequence | SEQ. ID No. | R4 Clone | Sequence | SEQ. ID No. | R5 Clone | Sequence | SEQ. ID No. | R6 Clone | Sequence | SEQ. ID No. |
|---|---|---|---|---|---|---|---|---|---|---|---|
| 1oprF1FAR3 | LISMQSR | 33 | 1oprF1FAR4 | QMLLRLP | 31 | 1oprF1FAR5 | LQTNPSM | 47 | 1oprF1FAR6 | PPKINIM | 6 |
| 2oprF1FAR3 | IRLRKHT | 34 | 2oprF1FAR4 | NLPMSRR | 43 | 2oprF1FAR5 | PIKTNRK | 27 | 2oprF1FAR6 | ** | — |
| 3oprF1FAR3 | RNRMRRL | 35 | 3oprF1FAR4 | IQLKINS | 7 | 3oprF1FAR5 | PPKINIM | 6 | 3oprF1FAR6 | IQTNPTM | 14 |
| 4oprF1FAR3 | RRIPLQL | 36 | 4oprF1FAR4 | IRLRKHT | 34 | 5oprF1FAR5 | PIKTNRK | 27 | 4oprF1FAR6 | PPKINIM | 6 |
| 5oprF1FAR3 | IHRMIHR | 37 | 5oprF1FAR4 | IRNITSH | 44 | 6oprF1FAR5 | NKMPRSM | 48 | 5oprF1FAR6 | PPKINIM | 6 |
| 6oprF1FAR3 | ** | — | 6oprF1FAR4 | RRSTSRQ | 39 | 7oprF1FAR5 | SRNQSRL | 5 | 6oprF1FAR6 | RGQSQPS | 52 |
| 7oprF1FAR3 | QMLLRLP | 31 | 7oprF1FAR4 | QMLLRLP | 31 | 8oprF1FAR5 | PPKINIM | 6 | 7oprF1FAR6 | PPKINIM | 6 |
| 8oprF1FAR3 | MNIKTKI | 38 | 8oprF1FAR4 | PIKRNRK | 27 | 9oprF1FAR5 | TSLTTSP | 49 | 8oprF1FAR6 | PPKINIM | 6 |
| 9oprF1FAR3 | IQTNPTM | 14 | 9oprF1FAR4 | IQTNPTM | 14 | 10oprF1FAR5 | PPKINIM | 6 | 9oprF1FAR6 | SPRTSRN | 39 |
| 10oprF1FAR3 | RRSNSQL | 13 | 10oprF1FAR4 | PKRTPRH | 22 | 11oprF1FAR5 | PPKINIM | 6 | 10oprF1FAR6 | PPKINIM | 6 |
| 11oprF1FAR3 | SPRTSRN | 39 | 11oprF1FAR4 | ** | — | 12oprF1FAR5 | PPKINIM | 6 | 12oprF1FAR6 | PPKINIM | 6 |
| 12oprF1FAR3 | QITLRST | 40 | 12oprF1FAR4 | KNMPRSM | 45 | 13oprF1FAR5 | RNRLTLP | 50 | 13oprF1FAR6 | NIQVGQP | 53 |
| 13oprF1FAR3 | QNLTRNI | 41 | 13oprF1FAR4 | PPKINIM | 6 | 14oprF1FAR5 | PPKINIM | 6 | 14oprF1FAR6 | NKMPRSM | 48 |
| 14oprF1FAR3 | IIPPLRR | 42 | 14oprF1FAR4 | PLRRNIL | 46 | 15oprF1FAR5 | PPKINIM | 6 | 15oprF1FAR6 | PPKINIM | 6 |
| 15oprF1FAR3 | QITLRST | 40 | 15oprF1FAR4 | ** | — | 16oprF1FAR5 | KIPTLIN | 51 | 16oprF1FAR6 | PPKINIM | 6 |

TABLE 4

| Unamplified clone | Sequence | SEQ. ID No. |
|---|---|---|
| A1 | RRSNSQL | 13 |
| A2 | PIKTNRK | 27 |
| A3 | SRNQSRL | 5 |
| A4 | RRSNSQL | 13 |
| A5 | SRNQSRL | 5 |
| A6 | QITLRST | 40 |
| A7 | QITLRST | 40 |
| A8 | RRSNSQL | 13 |
| A9 | SRNQSRL | 5 |
| A10 | RRSNSQL | 13 |
| A11 | RRSNSQL | 13 |
| A12 | IRLRKHT | 34 |
| A13 | PPKINIM | 6 |
| A14 | NMTNPPP | 10 |
| A15 | RRSNSQL | 13 |
| A16 | RRSNSQL | 13 |
| A17 | QMLLRLP | 31 |
| A18 | NMTNPPP | 10 |
| A19 | IQTNPTM | 14 |
| A20 | NMTNPPP | 10 |
| A21 | SRNQSRL | 5 |
| A22 | QITLRST | 40 |
| A23 | PIKTNRK | 27 |
| A24 | RRSNSQL | 13 |
| A25 | LRRIPRN | 21 |
| A26 | RRSNSQL | 13 |
| A27 | RRSNSQL | 13 |
| A28 | PIKTNRK | 27 |
| A29 | PKRTPRH | 22 |
| A30 | LRRIPRN | 21 |

The phage library was then screened to identify target-unrelated peptides by using biotinylated bovine serum albumin ("BSA") as a target for biopanning. In addition to the PPKINIM (SEQ. ID No. 6) phage, another bacteriophage, displaying the IQTNPTM (SEQ. ID No. 14) peptide, was found to cross-react with BSA (see Table 5, below).

TABLE 5

| Round 3 Clone | Sequence | SEQ. ID No. |
|---|---|---|
| 1 BSA R3 | KRSHLIR | 54 |
| 2 BSA R3 | HQSRHMI | 55 |
| 3 BSA R3 | IQTNPTM | 14 |
| 4 BSA R3 | LPQRLRT | 56 |
| 5 BSA R3 | ILRHPHT | 57 |
| 6 BSA R3 | NRNLPQL | 58 |
| 7 BSA R3 | SQRRTRI | 29 |
| 8 BSA R3 | KNIRKTI | 60 |
| 9 BSA R3 | TTRHINR | 61 |
| 12 BSA R3 | PPKINIM | 6 |
| 13 BSA R3 | IRMSRTK | 62 |
| 14 BSA R3 | SINQRRP | 63 |
| 15 BSA R3 | TIRKKNL | 64 |
| 16 BSA R3 | TIRKKNL | 64 |
| 17 BSA R3 | RRPRISH | 65 |
| 18 BSA R3 | PRMLPMI | 66 |

Collectively, stringent biopanning and library screening allowed us to select six unique heptapeptides for fluorescent probe synthesis and evaluation of bacterial detection (Table 6, below).

The binding of multiple BREs (i.e., OBP4 through OBP12) to OprF1 were assessed by Western blot analysis. Monoclonal OprF-specific bacteriophages were incubated with biotinylated OprF1 (OprF1-B) peptide epitope under conditions similar to those used in biopanning. The resulting phage-OprF1-B complexes were recovered using streptavidin-coated magnetic beads, and the phage-OprF1-B complexes were resolved via SDS-PAGE and detected by Western blot using antibodies against the M13 phage capsid and the biotin molecule attached to OprF1.

TABLE 6

| Sequence # | Peptide ID | Peptide Sequence | pI | % Abundance | Fluorescence (RFU) |
|---|---|---|---|---|---|
| 13 | OBP4 | R R S N S Q L | 12.0 | 33 | 4520 ± 473 |
| 10 | OBP6 | N M T N P P P | 5.5 | 10 | 2080 ± 280 |
| 40 | OBP7 | Q I T L R S T | 9.8 | 10 | 2625 ± 543 |
| 31 | OBP9 | Q M L L R L P | 9.8 | 3 | 3338 ± 590 |

TABLE 6-continued

| Sequence # | Peptide ID | Peptide Sequence | pI | % Abundance | Fluorescence (RFU) |
|---|---|---|---|---|---|
| 27 | OBP11 | P I K T N R K | 11.2 | 10 | 5308 ± 501 |
| 22 | OBP12 | P K R T P R H | 12.0 | 3 | 6443 ± 957 |

TABLE 7

| Sequence # | Peptide ID | Peptide Sequence | pI | % Abundance | Fluorescence (RFU) |
|---|---|---|---|---|---|
| 67 | OPP1 | P R I R K S H | 12.0 | 3 | 12258 ± 2060 |
| 68 | OPP2 | M H N L N L L | 6.5 | 2 | 1847 ± 52 |
| 69 | OPP3 | L P S T I H R | 9.8 | 2 | 2251 ± 63 |
| 70 | OPP4 | L R P L M N R | 12.0 | 3 | 1383 ± 74 |
| 71 | OPP5 | I I T M K R R | 12.0 | 3 | 4408 ± 225 |
| 72 | OPP6 | R K K S R I R | 12.3 | 2 | 4126 ± 98 |

Western blotting was performed by preparing a 200 µL solution with each of the phage clones at a concentration of 1×10$^{11}$ pfu/mL in 1×TBS, pH 7.5. Then, 10 µL of OprF1-biotin target peptide of concentration 1 mg/mL was added to each phage solution and incubated at 25° C. for 1 hr. Phage-OprF Biotin complexes were captured and pull-down with 25 µL of streptavidin-coated beads, and the captured complexes washed five times with 1×TBST. The pelleted complexes were re-suspended in 20 µL of 2× Laemmli Buffer, heated to 95° C. for 5 min, and resolved in a 14% SDS-PAGE gel. Proteins were blotted to a nitrocellulose membrane and blocked with TBST containing 5% BSA. To detect phages, a 1:2000 dilution of rabbit anti-M13 phage antibody (primary antibody) followed by a 1:5000 dilution of alkaline phosphatase (AP)-conjugated goat anti-rabbit antibody was used. For detection of biotinylated OprF1, a 1:2000 dilution of AP-conjugated goat anti-biotin antibody was used. For colorimetric visualization, BCIP/NBT reagent was used. In the M13 phage detection and OprF1-biotin detection, positive controls 10 µL of 9×10$^{12}$ pfu/mL wild type M13 phage in 10 µL 2× Laemmli Buffer and 20 µL of 1 mg/mL OprF1-biotin in 20 µL 2× Laemmli Buffer were used per well, respectively.

Figure 4:
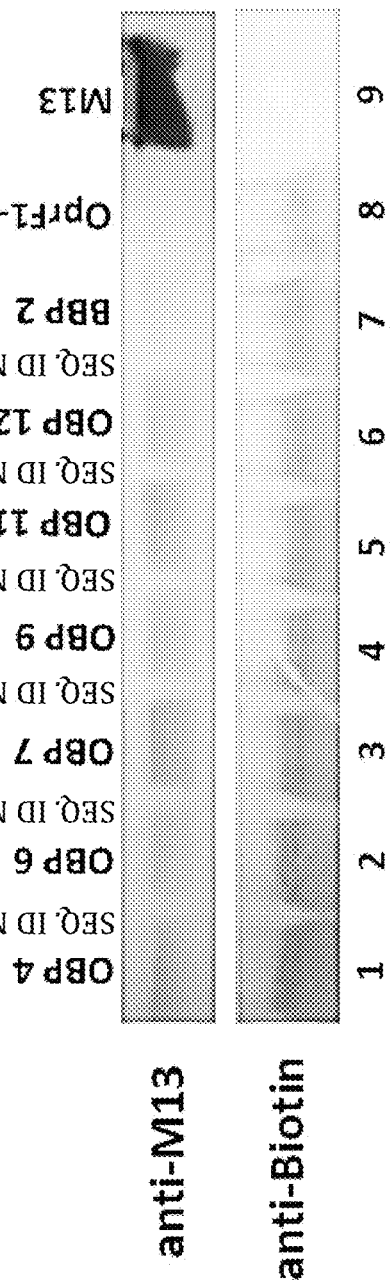
FIG. 4 is an image captured from a Western blot analysis of OprF-specific BREs.
Figure 5:
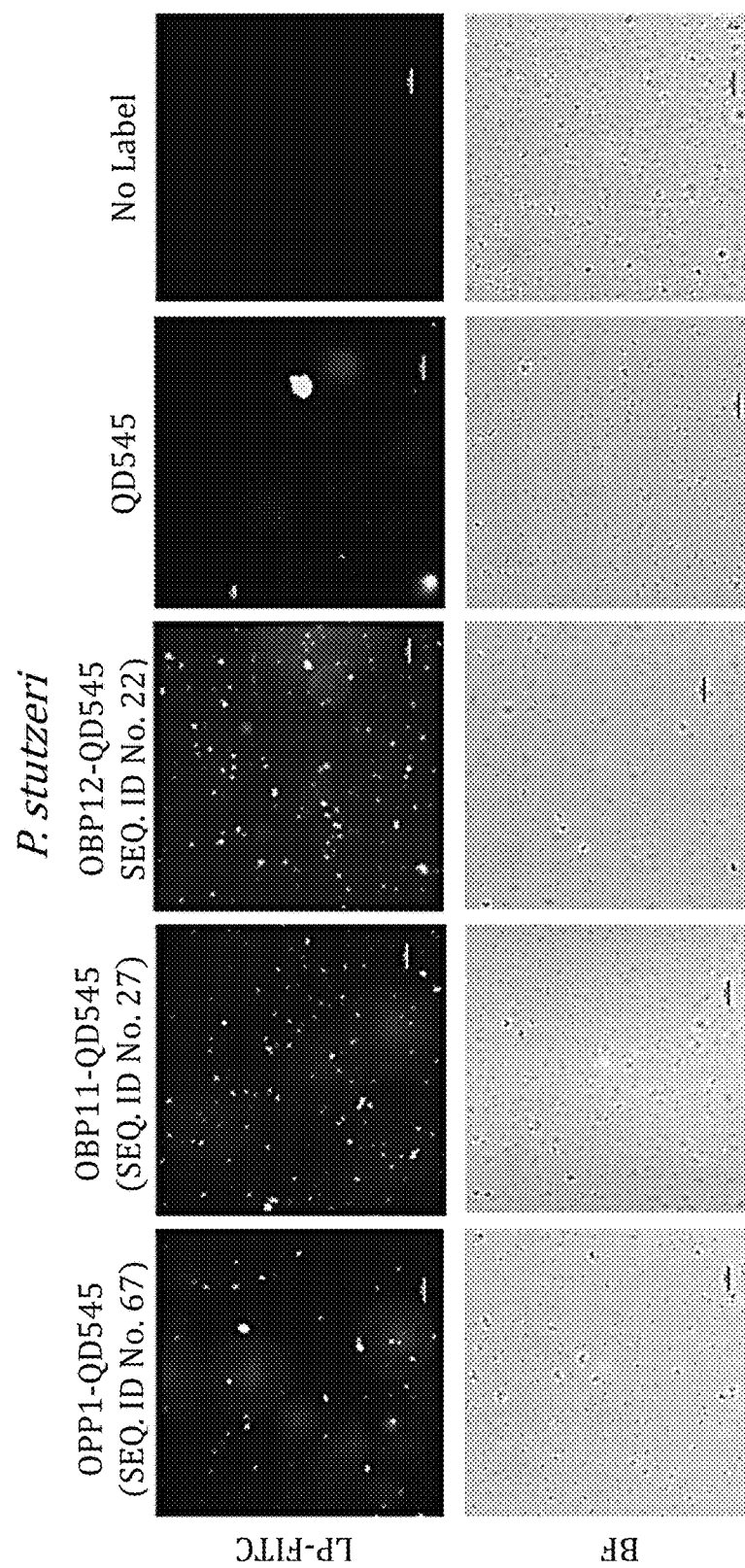
Figure 6:
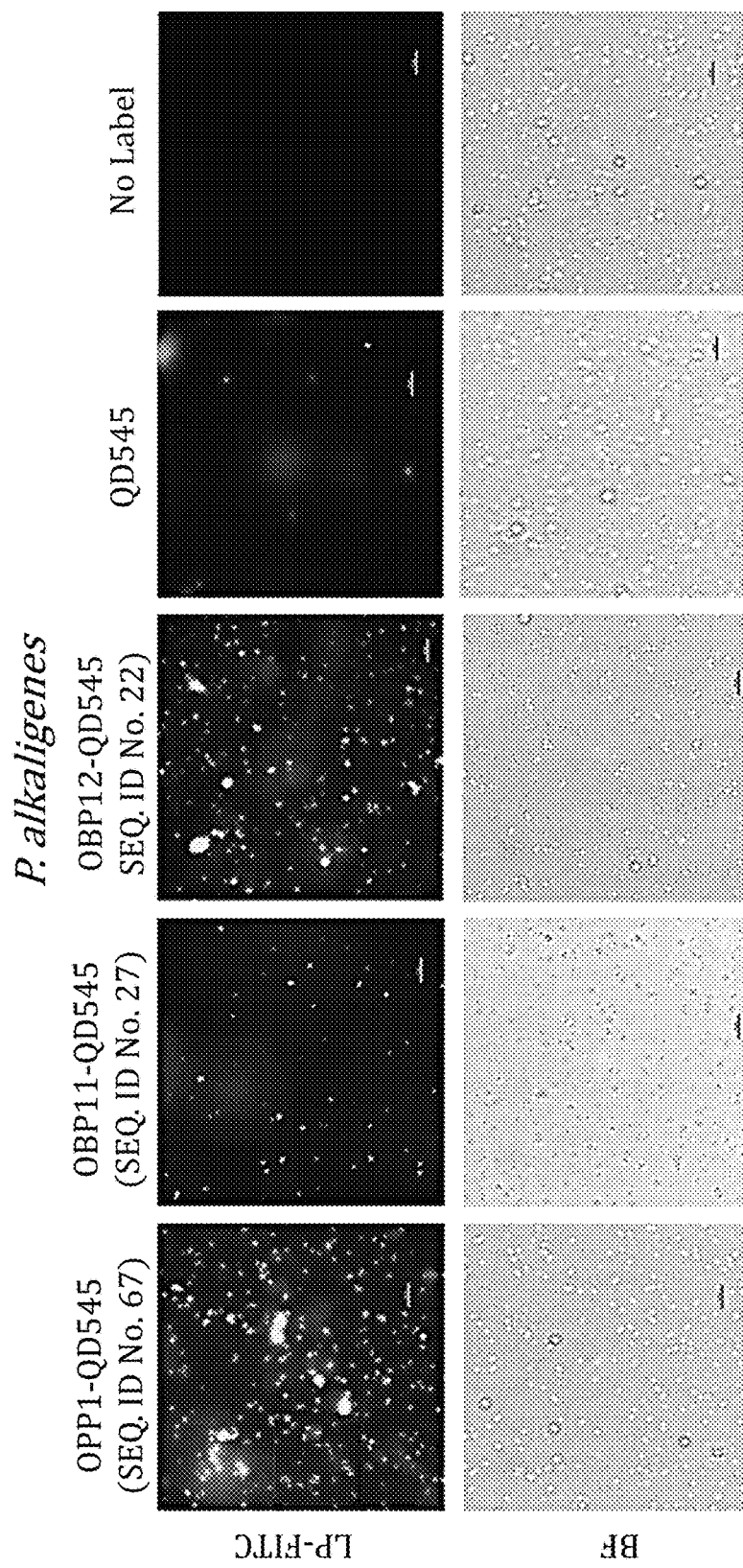
Figure 8:
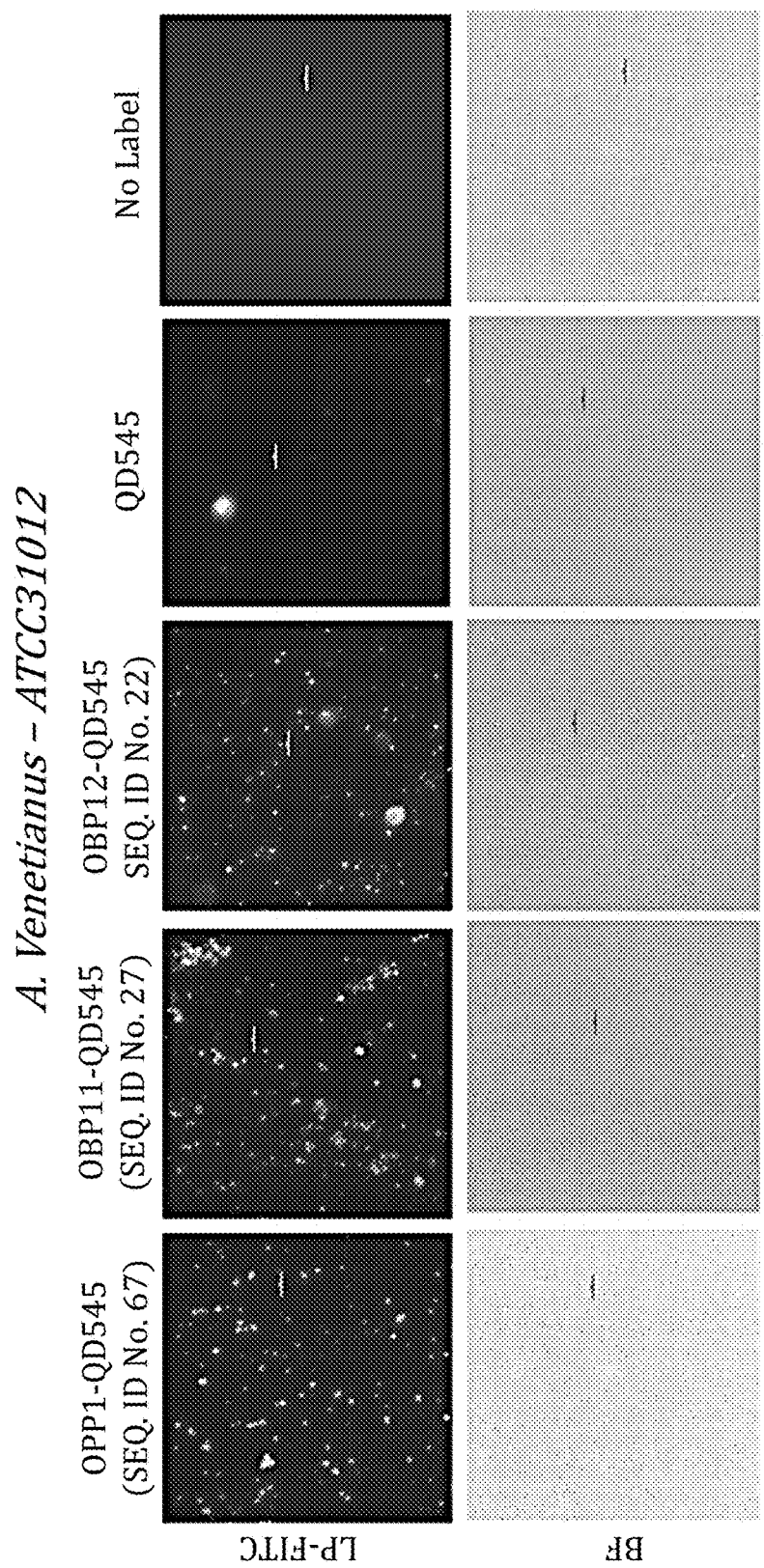
Figure 9:
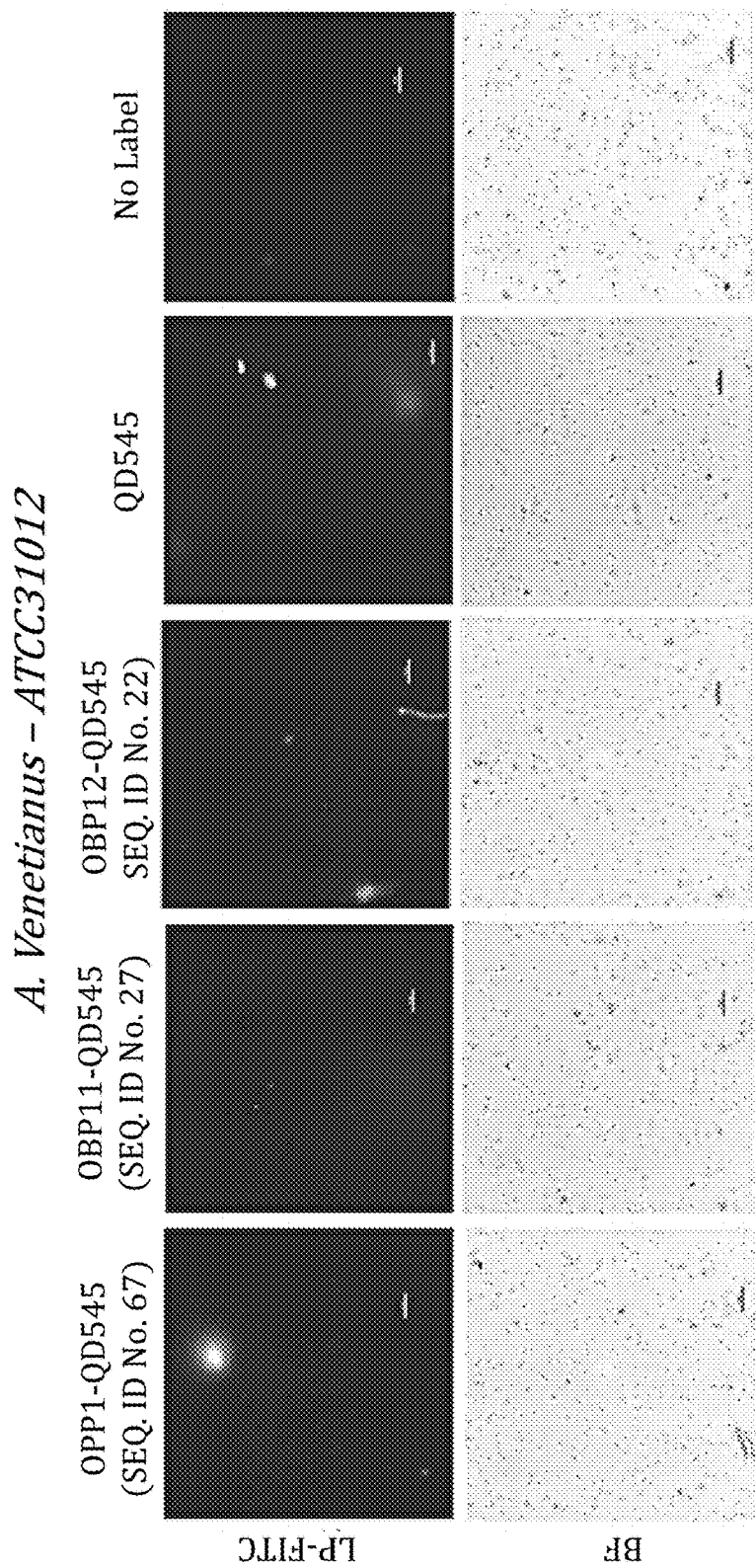
Figure 10:
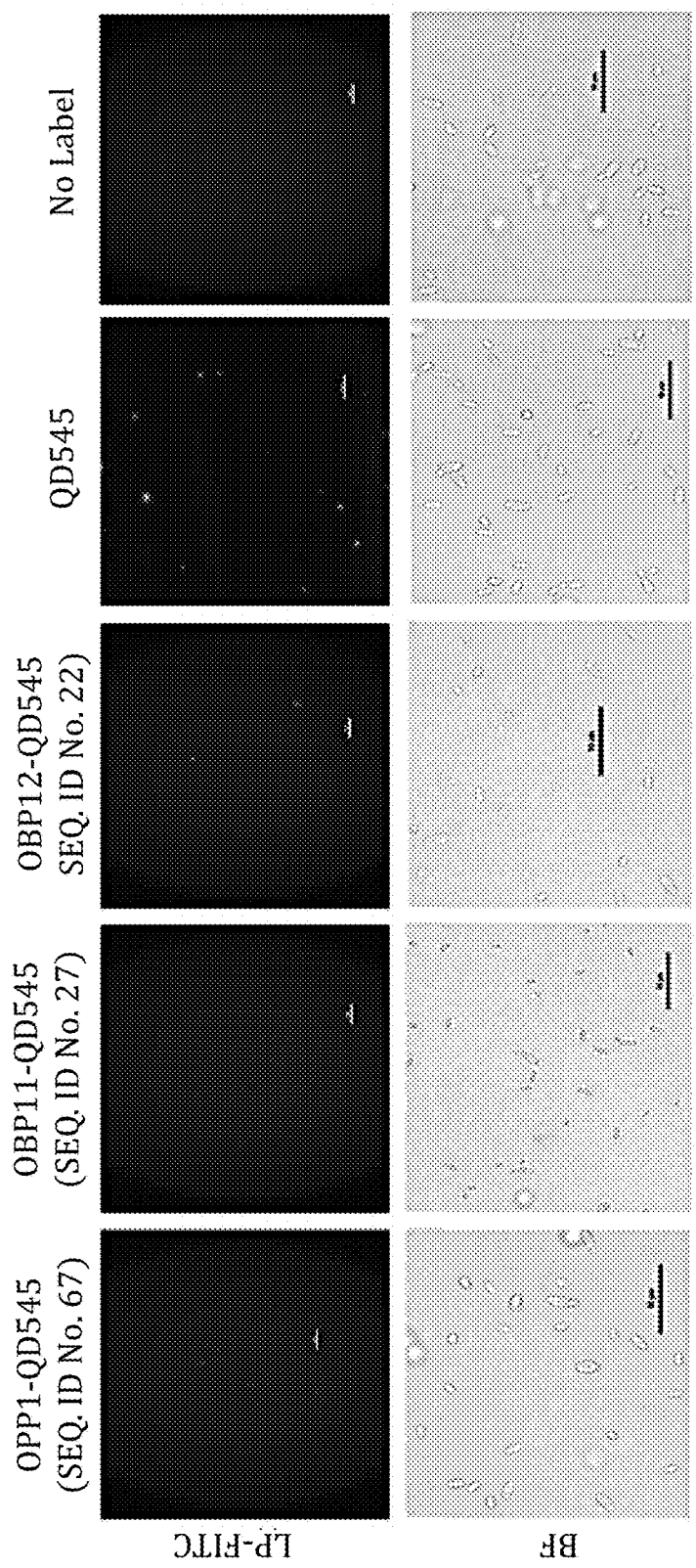

Monoclonal OprF-specific phages were shown to bind specifically to OprF1-Biotin, and both the phage and OprF1-Biotin were detected in immunoblots (FIG. 4). When phages with specificity for BSA were used against the OprF1-Biotin target, signal was not detected in the immunoblots, which suggests that complexing specificity were due to the OprF1-specific peptides and not due to non-specific binding of M13 phage capsid proteins and non-target library peptides.

Example 2

Having established an effective biopanning protocol with OprF to select BREs against *Pseudomonas*, the procedure was applied to develop BREs with the broader specificity of detecting multiple Gram negative genera. To do so, the Opr86 outer membrane protein was targeted. The Opr86 external loop fragment spanning aa668 to aa683 is a highly immunogenic epitope that could be used in the isolation of *Pseudomonas* specific antibodies. Moreover, an as sequence alignment analysis performed on the aa668 to aa683 region of the Opr86 external loop from different species revealed this region consisted of 35 highly conserved aa residues (aa630 to aa665) presenting more than 86% sequence homology among several *Pseudomonas* species (Table 8, below), and more than 50% sequence homology among various Gram negative bacteria (Table 9, below).

The particular region of the Opr86 extracellular loop of sequence YGSTDGLPFYENYYAGGFNSVRGFKDSTLG-PRSTP (SEQ. ID No. 3) was chemically synthesized with a biotin capture element and used as target epitope for BRE development in solution biopanning in Bushnell-Haas, pH 8.5, supplemented with 1% Jet-A. Following the previously established procedure for OprF, several unique Opr86 peptide BREs ("OPPs") were identified after three rounds of selection (Table 7, above).

The emission peak fluorescence at 525 nm of 1×10$^9$ *P. stutzeri* cells labeled with peptide-QD525 conjugates was measured in a fluorometer and relative fluorescence units ("RFIU") were compared (Table 6 and 7, above). Peptides OBP11 and OBP12 targeting OprF, and peptide OPP1 targeting Opr86 presented fluorescence levels that greatly surpassed the other selected peptides for the respective target. OPP1, OBP11, and OBP12 were selected for further characterization and validation.

TABLE 8

| | Sequence # | - - - - - - - - - - 10- - - - - - - - - - 20- - - - - - - - - - 30- - - - - |
|---|---|---|
| Opr86 | 3 | Y G S T D G P L F Y E N Y Y A G G F N S V R G F K D S T L G P R S T P |
| *P. aeruginosa* | 73 | Y G S T E R L P F Y E N Y Y A G G F N S V R G F K D S T L G P R S T P |

TABLE 8-continued

| Sequence # | | 10 | 20 | 30 | |
|---|---|---|---|---|---|
| P. stutzeri | 74 | Y G S T S R L P F Y | E H Y Y A G G F N S | V R G F E D S S L G P R S T P | |
| P. fluorescens | 75 | Y G S T D G L P F Y | E N Y T A G G E G S | V R G F E S G T L G P R N T P | |
| P. putida | 76 | Y G S T D G L P F Y | E S Y N A G G Q G S | V R G F K D G T L G P P S T P | |
| Consistency | – | * * * * 6 5 * * * * | * 6 * 4 * * * 4 6 * | * * * * 7 7 6 8 * * * * 8 * * | |

TABLE 9

| Sequence # | | 10 | 20 | 30 | |
|---|---|---|---|---|---|
| Opr86 Fragment | 3 | Y G S T D G L P F Y | E N Y Y A G G F N S | V R G F K D S T L G P R S T P | |
| Achromobacter | 77 | Y G S K D - Y P I I | K N V Y A G G I G T | V R G Y E G S S L G P R D S K | |
| Ralstonia | 78 | Y G G K D - F P V F | K N Y Y A G G I G S | V R G Y E T S T L G P R D A N | |
| E. coli | 79 | L G G K E - M P F Y | E N F Y A G G S S T | V R G F Q S N T I G P K A V Y | |
| Acinetobacter | 80 | - - - - N D L P F Y | K N F Y A G G Y G S | V R G Y D N S S L G P K Y P S | |
| Consistency | – | 3 6 3 4 6 0 5 * 5 5 | 7 * 5 * * * * 4 6 7 | * * * 8 6 4 8 7 9 * * 8 3 4 2 | |

Example 4

Figure 11:
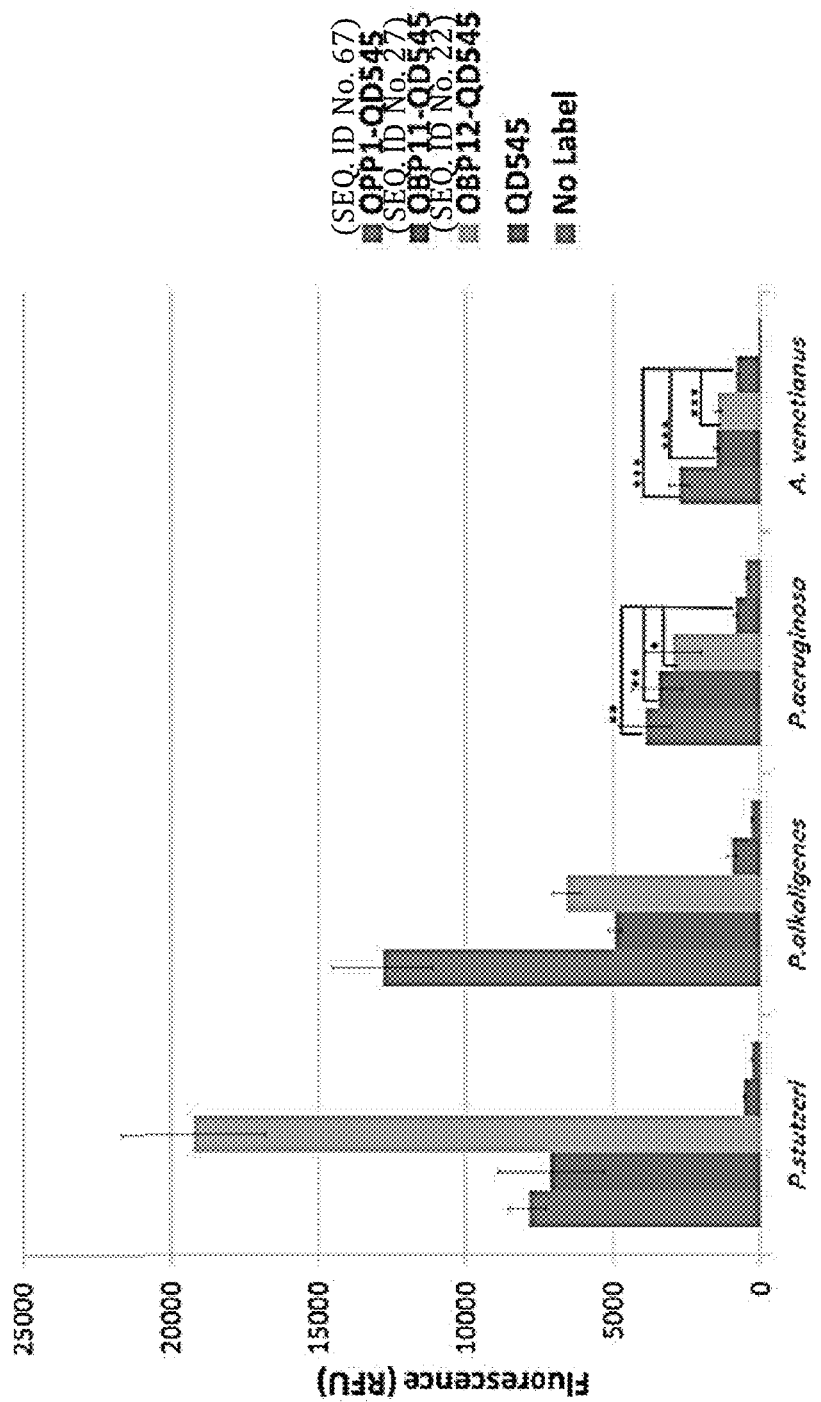
FIG. 11 is a graphical representation of fluorometry of *A. venetianus* and *Pseudomonas* spp. Labeled with peptide-QD545 conjugates.

To characterize the specificity of the peptide BRE-QD545 conjugates for the intended bacterial groups, fluorescence imaging and fluorometric analysis were performed using different Gram negative and Gram positive fuel degrading bacteria. As such, cultures comprising 1×10⁹ cells of Gram negative bacteria (*P. stutzeri, P. alkaligenes, P. aeruginosa* and *A. venetianus*) and Gram positive bacteria (*Arthrobacter* sp. and *Lynsinibacillus* sp.) were labeled with OPP1, OBP11 and OBP12 biofunctionalized QD545 and visualized using fluorescence microscopy (FIGS. 5-10) and the fluorescence quantified using a fluorometer (FIG. 11).

Bacterial stocks for experimentation were prepared by harvesting overnight grown bacterial cells by centrifugation at 11000×g for 15 min (at 4° C.), washed once with 1×PBS, pH 7.2, and re-suspended in 1×PBS to a concentration of 1×10⁹ cells/mL. Bacterial titers were determined by measuring optical density at 600 nm and confirmed by colony counting on LB agar plates. Cell pellets produced by centrifuging 1 mL of the 1×10⁹ cells/mL stock were re-suspended in 38 µL of 1×PBS and 62 µL of 2.4 µM peptide-QD was added to a final concentration of 1.5 µM. Cells were incubated for 30 min at 25° C. Cell pellets were washed three-times with 0.5 mL PBS and re-suspended in 500 µL PBS for fluorescence assays and imaging. Dilutions ranging from 1×10⁹ cells to 1×10⁴ cells were prepared using standard bacteriological techniques and 0.5 mL samples were used for fluorescence measurements.

Emission spectra were obtained using Cary Eclipse Fluorimeter with excitation at 330 nm, scan rate of 120 nm/imin, and PMT voltage of 1000V. Spectra were corrected for background and dilution factor when appropriate.

10 µL of the prepared sample was placed on a microscope slide, covered with a coverslip, and visualized on an Nikon Eclipse Ti-E inverted microscope equipped with X-Cite LED lamp, a fluorescence filter set (a bandpass exciter 405 nm and a longpass emission filter), a 1.25-numerical-aperture oil-immersion objective (DPlan 100×, Nikon). Images were captured by Nikon DS-sCMOS camera.

The fluorescence micrographs showed that OPP1, OBP11, and OBP12 specifically labeled Gram negative bacteria but not the Gram positive bacteria, which do not contain OprF and Opr86 outer membrane proteins. The presence of a high number of bacteria in all treatments was confirmed by bright field imaging (FIGS. 5-10).

To determine whether QDs that have not been biofunctionalized with the peptide BREs did not bind to the bacteria cells, all bacterial species were exposed to QD545 at an equal concentration to the peptide-QD545 conjugates used in testing. The results showed a lack of bacterial fluorescence from the QD545 treatment and from the unlabeled cells negative control. Careful analysis of the fluorescence micrographs showed that only the cell wall of Gram negative bacteria was fluorescently stained. Labeled cells appeared dark in the center with highly fluorescent outer membranes. These results confirmed localization of the fluorescent labeling and the specificity of BRE-QD conjugates for the OprF and Opr86 outer membrane components of the Gram negative cell wall. Also observed was that biofilms produced by *Pseudomonas* species, especially in *P. aeruginosa*, were labeled in addition to the planktonic cells. Fuel-degrading bacteria, such as *P. aeruginosa*, produce biofilms, especially at the fuel-water interface, as protection from the toxic fuel environment and access the hydrocarbons in the fuel. These results suggested that peptide biofunctionalized QDs may be used to detect bacterial species during different growth stages in the fuel system.

As shown in FIG. 11, OPP1-QDs provided high fluorescence levels with all Gram negative bacteria tested and were the conjugate that best detected *A. venetianus* and *P. alkaligenes* bacteria. This result confirmed that the external loop region of Opr86 indeed was highly conserved among different Gram negative bacteria. Both, OBP11 and OBP12 were able to detect all Gram negative bacteria tested and provided the acinetobest detection against Pseudomonads.

Figure 12:
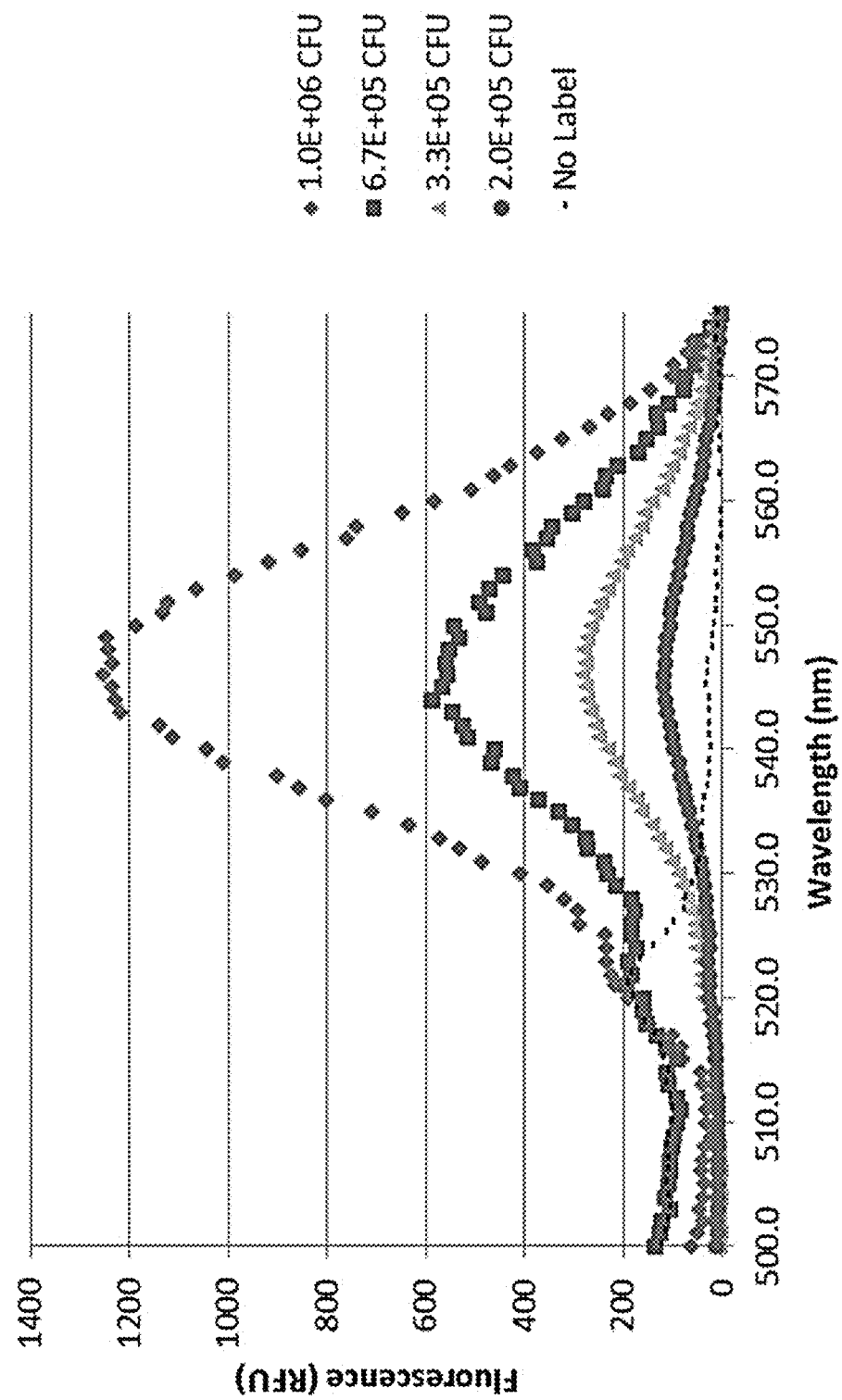
FIG. 12 is a graphical representation of fluorescence signal linearity from labeled cells.

OBP12 presented the highest LOD of *P. stutzeri* among all the BREs. Only baseline fluorescence below 25 RFU was detected in un-labeled cells and cells exposed to non-biofunctionalized QDs. A test performed to characterize the linearity of the fluorescence signal from peptide-QDs demonstrated the fluorescence signal intensity approximately doubled with each doubling in cell concentration (FIG. 12).

Example 5

To test the applicability of the peptide BRE-QD chemistry in the detection of bacteria in fuel and characterize the LOD in such system, bacterial cells from 1 L jet fuel samples spiked with different levels of bacteria were recovered, labeled, and detected.

*P. aeruginosa* ATCC33988 and *A. venetianus* ATCC31012 were purchased from American Tissue Culture Collection (Manassas, Va.). *P. stutzeri, P. alcalignes, Arthrobacter* sp., and *Lysinibacillus* sp. were isolated in the laboratory from fuel contaminated soil. *E. coli* 2738 was used from a commercially-available phage display kit (New England Biolabs, Ipswich, Mass.).

Overnight cultures of fuel degrading bacteria were grown in LB broth at 28° C. with shaking at 225 rpm. Stock cultures of all microbial strains were stored in 15% glycerol at −80° C. *E. coli* was grown at 37° C.

One liter Jet A fuel samples were amended with 1 mL of 1×PBS containing either *A. venetianus* ATCC 31012 or *P. stutzeri* at the appropriate test concentration was added to 1 L of Jet A fuel. The inoculated jet fuel samples were thoroughly mixed by vortex for 1 min and allowed to stand for 20 min to 30 min. To recover the cells, 1 mL of 1×PBS, named bacterial recovery solution ("BRS"), was added to the jet fuel samples, the samples shaken by hand, allowed stand for 5 min, and, then, 1 mL of the aqueous phase was collected using a long serological pipette. The 1 mL of solution with bacteria was centrifuged for 5 min at 11000×g, and washed three times with 1 mL of 1×PBS. Bacterial pellets were individually labeled using a final concentration 1.5 µM peptide-QD. The LOD was defined as the lowest concentration level that could be determined to be statistically different from QD labeled cells from the results of multiple testers. The actual cell level (colony-forming units, "CFU") detected was determined by plating a portion of the sample after being subjected to the labeled procedure.

Figure 13:
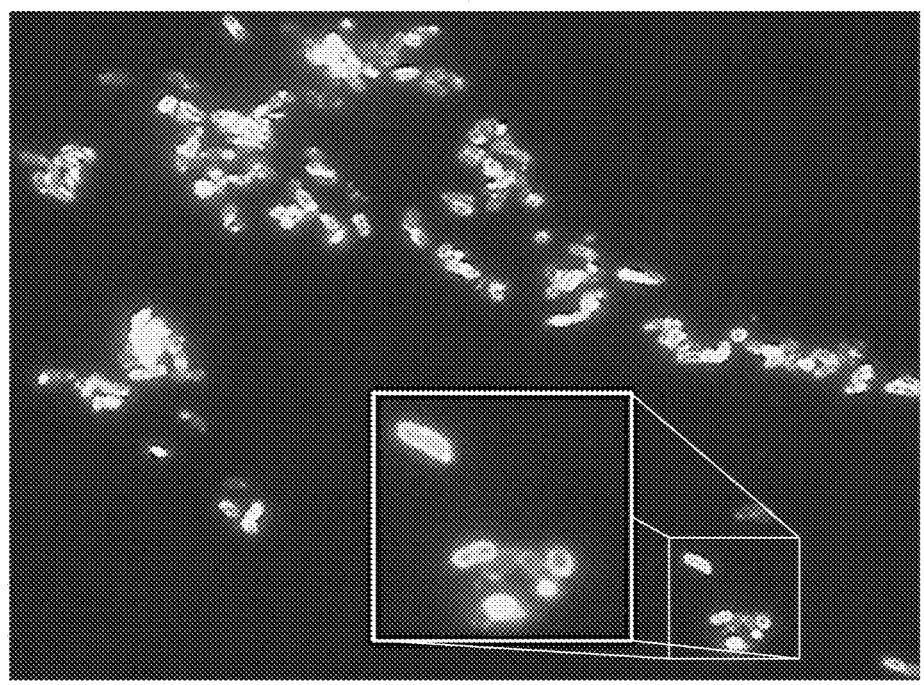
FIG. 13 is an exemplary image of *Pseudomonas* of a fuel sample labeled with peptide BRE-QD545.
Figure 14:
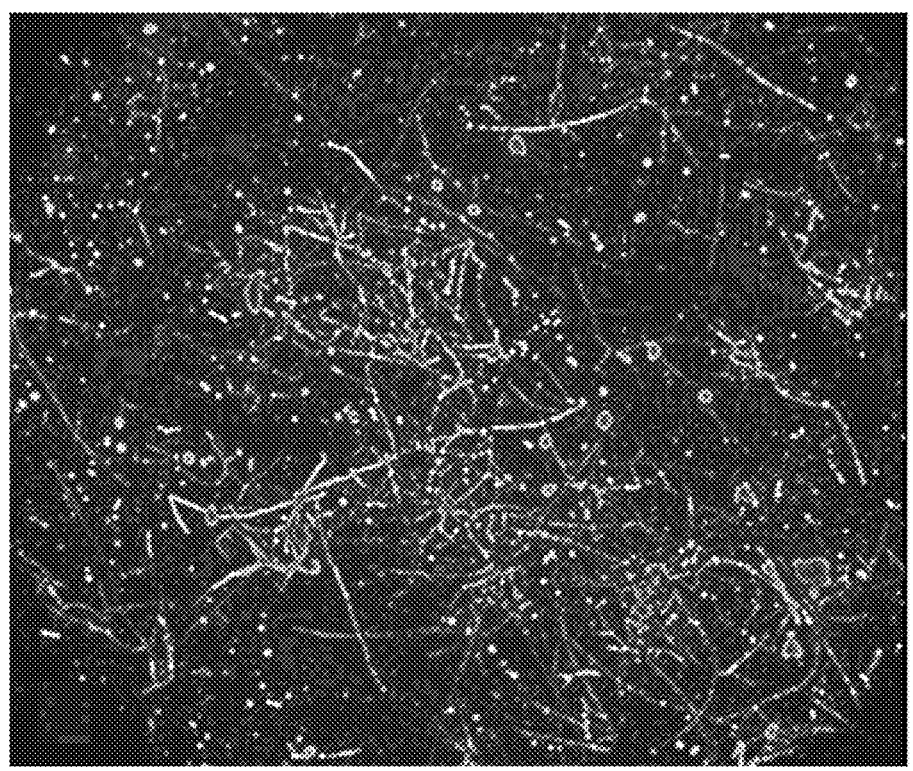
FIG. 14 is an exemplary image of a fungus (*Hormoconis*) labeled with peptide BRE-QD605.

Cells in the 1 L of fuel were recovered with 1 mL of BRS. Efficient labeling of the bacteria was indicated by high levels of fluorescence detected from the cell wall by fluorescence microscopy (FIG. 13 and Table 10, below). FIG. 14 is a similar image but of fungus (*Hormoconis*) labeled by peptide-QD605. The LOD was reliably determined from assays performed by multiple testers.

TABLE 10

| PEPTIDE-QD LABEL | BACTERIA | LOD (CFU) | FLUORESCENCE (RFU) |
| --- | --- | --- | --- |
| QD545-OBP12 | *P. stutzeri* | $5 \times 10^5$ | 12,205 |
| QD545-OBP11 | *P. stutzeri* | $5 \times 10^5$ | 255 |
| QD545-OPP1 | *P. stutzeri* | $5 \times 10^5$ | 820 |
| QD545-OBP12 | *A. venetianus* | $5 \times 10^5$ | 580 |
| QD545-OBP11 | *A. venetianus* | $5 \times 10^5$ | 292 |
| QD545-OPP1 | *A. venetianus* | $5 \times 10^5$ | 773 |

The OPP1-QD545 conjugate detected *P. stutzeri* and *A. venetianus* at an LOD of $5 \times 10^4$ CFU/mL of BRS and detection was possible down to $5 \times 10^3$ CFU/mL of BRS, in some instances. OBP11-QD545 and OBP12-QD545 presented a LOD of $5 \times 10^5$ CFU/mL of BRS for *P. stutzeri* and *A. venetianus*. In some instances, *P. stutzeri* and *A. venetiatus* were detected with OBP11-QD545 and OBP12-QD545 down to $5 \times 10^4$ CFU/mL of BRS, which indicates that the assay had the potential to be further optimized to detect much lower bacterial levels in fuel.

Differences in LOD between OPP1 and the two OBPs may be attributed to variability in Opr86 and OprF protein levels in the different bacterial strains, as well as structural and/or conformational differences in the external epitopes of Opr86 and OprF that may modulate the binding of BRE to the target epitope. Intrinsic variability in how the assay protocol was performed by the different testers and the use of multiple centrifugation steps in the protocol was credited for the detection fluctuations at cell levels below the reproducible LOD and for not achieving a much lower LOD. Lower LOD may be achieved by substituting all centrifugation steps with a single filter membrane to recover cells from the fuel, carryout all washes, and perform the detection step, all of which may prevent the loss of labeled bacteria, reduce background fluorescence, and improve the assay LOD.

Example 6

To test whether the BRE-QD chemistry could effectively detect bacteria within a fuel sample from the field, a contaminated jet fuel sample from a fuel tank was obtained. 1 mL of the water layer of the fuel sample was tested with OBP11, OBP12, and OPP1 BRE-QDs following methods according to embodiments disclosed herein.

Figure 15:
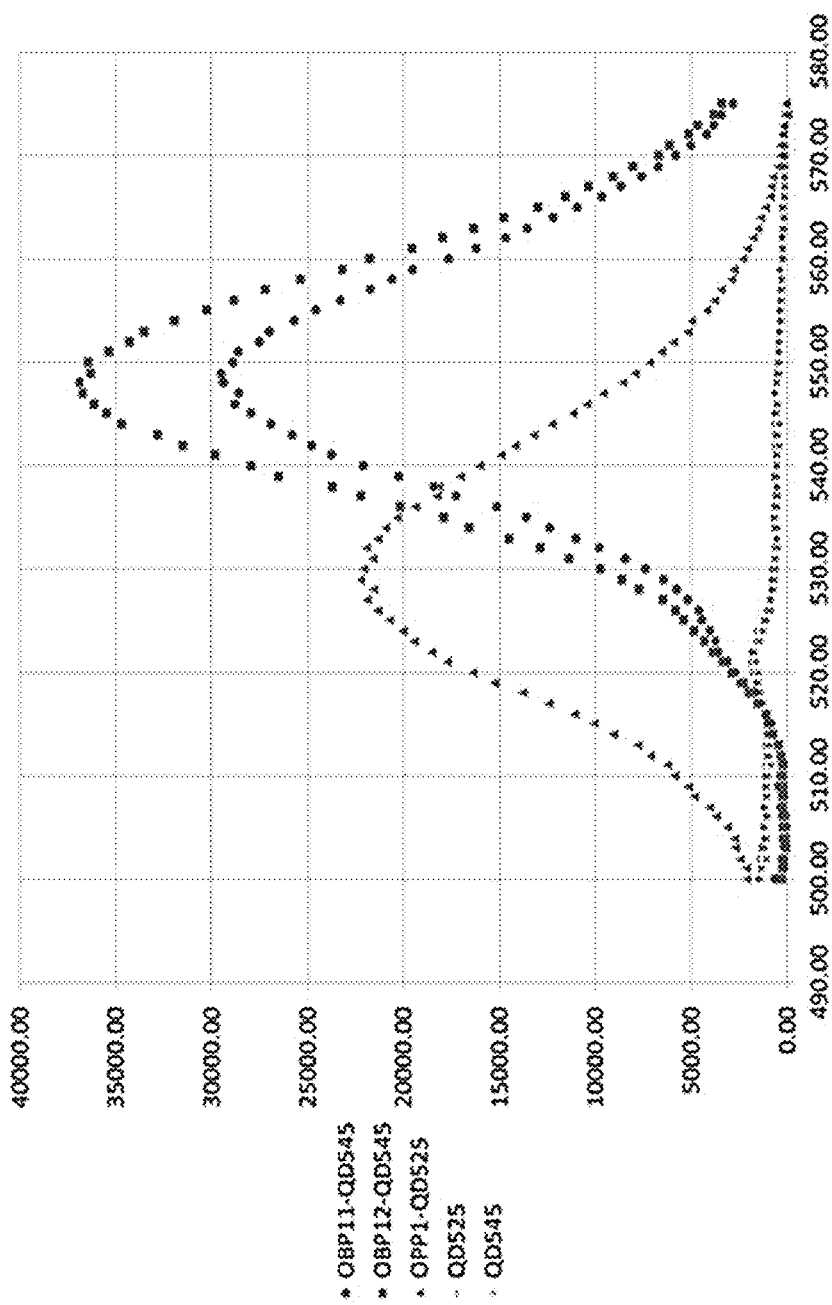
FIG. 15 is a graphical representation of fluorescence signal linearity from labeled cells It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

The fluorometer results showed very high fluorescent levels with all three peptide-QD assays ranging between 22,000 RFU and 37,000 RFU (see FIG. 15). The high fluorescence levels detected were an indication of heavy bacterial contamination in the fuel sample, which quantitatively may range between $1 \times 10$ CFU/mL and $1 \times 10^8$ CFU/mL.

To determine whether bacteria were present in the fuel sample, a bacterial contamination level was determined by quantitative real-time PCR ("qPCR", a nuclei acid-based molecular method) and by plate colony counting (a microbiological method). The qPCR method may detect culturable, non-culturable, and free DNA. Here, the qPCR results indicated $1.5 \times 10^6$ bacterial 16S gene copies/mL, which is considered to be a high level of contamination.

Colony counting, which quantified only culturable bacteria, detected about 80 CFU/mL. While the level of culturable bacteria was lower than expected, it is well known that bacteria adapted to the fuel environment may not form colonies in culture without prior acclimatization.

DNA sequencing of a 500 bp region of the bacterial 16S gene identified the isolated bacteria as *P. aeruginosa*. The high level of DNA detected with the well-established qPCR methods correlated well with the high RFU values provided by the peptide BRE-QD assay. This indicated the peptide BRE-QD chemistry and the established test method was suitable for quantification of Gram negative bacteria in fuel samples.

The methods described herein according to various embodiments thereof provide certain benefits of conventional methods, including the ability of the BREs described herein to target small biomolecules and epitopes that are conserved among large groups of fuel degrading microorganism and produced during growth in fuel. Additionally, the embodiments of the present invention provide peptide selection methods that were evaluated against changes in temperature, pH, and salt concentration so as to select those BREs that retain binding activity and specificity in the presence of hydrocarbon fuels. These BREs were selected and derived from the fundamental understanding of the adaptive mechanisms and biomolecules used and produced by hydrocarbon-degrading microorganisms during growth in fuel-containing environments. Embodiments of the present invention that include peptide-based devices provide accurate and quantitative real-time detection of microbial growth in fuel in the field (e.g., fuel samples, fuel tanks, pipelines) before high cell density is reached which leads to biofilms formation and biodeterioration.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A biorecognition element for detection of microbial biocontamination, the biorecognition element comprising:
SEQ. ID No. 10, SEQ. ID No. 13, SEQ. ID No. 22, SEQ. ID No. 27, SEQ. ID No. 31, SEQ. ID No. 40, SEQ. ID No. 67, SEQ. ID No. 68, SEQ. ID No. 69, SEQ. ID No. 70, SEQ. ID No. 71, or SEQ. ID No. 72;
an amine-functionalized quantum dot;
a C-terminal, three-glycine plus cysteine linker configured to cross-link to the amine-functionalized quantum dot; and
a reporter molecule conjugated to the amine-functionalized quantum dot.

2. The biorecognition element of claim 1, wherein the reporter molecule is a fluorescent molecule, a chemiluminescent molecule, a colorimetric molecule, or a signal transducing nanomaterial.

3. The biorecognition element of claim 1, wherein the microbial biocontamination is in a fuel phase or an aqueous phase of a fuel sample.

4. A method of detecting biocontamination, the method comprising:
acquiring a sample;
isolating microbes from the sample;
labeling the microbes with a first reporter, wherein the first reporter is conjugated to a biorecognition element selected from the group consisting of: SEQ. ID No. 10, SEQ. ID No. 13, SEQ. ID No. 22, SEQ. ID No. 27, SEQ. ID No. 31, SEQ. ID No. 40, SEQ. ID No. 67, SEQ. ID No. 68, SEQ. ID No. 69, SEQ. ID No. 70, SEQ. ID No. 71, and SEQ. ID No. 72.

5. The method of claim 4, wherein the sample is a fuel sample and isolating microbes further comprises:
moving microbes from a fuel phase of the fuel sample to an aqueous phase of the fuel sample;
drawing the aqueous phase from fuel phase; and
obtaining a microbe pellet by centrifugation of the aqueous phase.

6. The method of claim 4, wherein the sample is a fuel sample and isolating microbes from the fuel sample comprises:
filtering the microbes from a fuel phase of the fuel sample, an aqueous phase of the fuel sample, or both.

7. The method of claim 4, wherein the biorecognition element further comprises:
a C-terminal, three-glycine plus cysteine linker; and
an amine-functionalized quantum dot cross-linked to the three-glycine plus cysteine linker,
wherein the first reporter is conjugated to the amine-functionalized quantum dot.

8. The method of claim 4, wherein the first reporter is a fluorescent molecule, a chemiluminescent molecule, a colorimetric molecule, or a signal transducing nanomaterial.

9. The method of claim 4, further comprising:
labeling the microbes with a second reporter, wherein the second reporter is conjugated to a biorecognition element selected from the group consisting of: SEQ. ID No. 10, SEQ. ID No. 13, SEQ. ID No. 22, SEQ. ID No. 27, SEQ. ID No. 31, SEQ. ID No. 40, SEQ. ID No. 67, SEQ. ID No. 68, SEQ. ID No. 69, SEQ. ID No. 70, SEQ. ID No. 71, and SEQ. ID No. 72.

10. A biocontamination assay kit comprising:
a biorecognition element selected from the group consisting of: SEQ. ID No. 10, SEQ. ID No. 13, SEQ. ID No. 22, SEQ. ID No. 27, SEQ. ID No. 31, SEQ. ID No. 40, SEQ. ID No. 67, SEQ. ID No. 68, SEQ. ID No. 69, SEQ. ID No. 70, SEQ. ID No. 71, and SEQ. ID No. 72;
a C-terminal, three-glycine plus cysteine linker on the biorecognition element;
an amine-functionalized quantum dot cross-linked to the three-glycine plus cysteine linker; and
a reporter molecule conjugated to the amine-functionalized quantum dot.

11. The biocontamination assay kit of claim 10, further comprising:
a filter permeable to liquid and configured to retain microbes.

12. The biocontamination assay kit of claim 11, wherein the liquid is a fuel.

13. The biocontamination assay kit of claim 10, wherein the reporter molecule is a fluorescent molecule, a chemiluminescent molecule, a colorimetric molecule, or a signal transducing nanomaterial.

* * * * *

SEQUENCE LISTING

```
<160> NUMBER OF SEQ ID NOS: 80

<210> SEQ ID NO 1
<211> LENGTH: 11
<212> TYPE: PRT
<213> ORGANISM: Pseudomonas aeruginosa

<400> SEQUENCE: 1

Gly Thr Tyr Glu Thr Gly Asn Lys Lys Val His
1               5                   10

<210> SEQ ID NO 2
<211> LENGTH: 19
<212> TYPE: PRT
<213> ORGANISM: Pseudomonas aeruginosa

<400> SEQUENCE: 2

Ala Asp Ile Lys Asn Leu Ala Asp Phe Met Lys Gln Val Pro Ser Thr
1               5                   10                  15

Ser Thr Thr

<210> SEQ ID NO 3
<211> LENGTH: 35
<212> TYPE: PRT
<213> ORGANISM: Pseudomonas aeruginosa

<400> SEQUENCE: 3

Tyr Gly Ser Thr Asp Gly Leu Pro Phe Tyr Glu Asn Tyr Tyr Ala Gly
1               5                   10                  15

Gly Phe Asn Ser Val Arg Gly Phe Lys Asp Ser Thr Leu Gly Pro Arg
            20                  25                  30

Ser Thr Pro
        35

<210> SEQ ID NO 4
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 4

Asn Arg Asn Ile Arg Ile His
1               5

<210> SEQ ID NO 5
<211> LENGTH: 7
<212> TYPE: PRT
<213> ORGANISM: Artificial Sequence
```

```
<220> FEATURE:
<223> OTHER INFORMATION: Artificial sequence obtained through
      biopanning.

<400> SEQUENCE: 5

Ser Arg Asn Gln Ser Arg Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 6

Pro Pro Lys Ile Asn Ile Met
1               5

<210> SEQ ID NO 7
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 7

Ile Gln Leu Lys Ile Asn Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 8

Arg Thr Arg Arg Lys Ser Asn
1               5

<210> SEQ ID NO 9
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 9

Ile Leu Lys Ser Ile Thr His
1               5

<210> SEQ ID NO 10
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 10

Asn Met Thr Asn Pro Pro Pro
1               5
```

<210> SEQ ID NO 11
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 11

Asn Thr Arg Thr Met Ile Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 12

Ile Lys Pro Thr Asn Arg Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 13

Arg Arg Ser Asn Ser Gln Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 14

Ile Gln Thr Asn Pro Thr Met
1               5

<210> SEQ ID NO 15
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 15

Ser Leu Gln His Leu Arg Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Artificial sequence obtained through
      biopanning.

```
<400> SEQUENCE: 16

Arg Pro Arg Ile Ser Ile Ile
1               5

<210> SEQ ID NO 17
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 17

Ser Thr Pro Ile Ser Leu Leu
1               5

<210> SEQ ID NO 18
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 18

Lys Leu Asn Leu Met Arg Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 19

Met Lys Leu Ile Ile Arg Met
1               5

<210> SEQ ID NO 20
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 20

Pro Arg Arg Asn Arg Pro Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 21

Leu Arg Arg Ile Pro Arg Asn
1               5

<210> SEQ ID NO 22
<211> LENGTH: 7
<212> TYPE: PRT
```

```
<213> ORGANISM: Artificial Sequence
<220> FEATURE:
<223> OTHER INFORMATION: Artificial sequence obtained through
      biopanning.

<400> SEQUENCE: 22

Pro Lys Arg Thr Pro Arg His
1               5

<210> SEQ ID NO 23
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 23

Pro Lys Arg Arg Ser Gln Asn
1               5

<210> SEQ ID NO 24
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 24

Met Leu Leu Met Thr Pro His
1               5

<210> SEQ ID NO 25
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 25

Pro Asn Arg Arg Ser Arg Ser
1               5

<210> SEQ ID NO 26
<211> LENGTH: 6
<212> TYPE: PRT
<213> ORGANISM: Artificial Sequence
<220> FEATURE:
<223> OTHER INFORMATION: Artificial sequence obtained through
      biopanning.

<400> SEQUENCE: 26

Met Thr Arg Gln Ser Ile
1               5

<210> SEQ ID NO 27
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 27

Pro Ile Lys Thr Asn Arg Lys
1               5
```

```
<210> SEQ ID NO 28
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 28

Met Pro Met Met Leu Met Met
1               5

<210> SEQ ID NO 29
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 29

Leu Leu Arg Met Arg His Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 30

Ile Lys Thr Ser His Pro Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 31

Gln Met Leu Leu Arg Leu Pro
1               5

<210> SEQ ID NO 32
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 32

Pro Ser Gln Arg Met Thr Met
1               5

<210> SEQ ID NO 33
<211> LENGTH: 7
<212> TYPE: PRT
<213> ORGANISM: Artificial Sequence
<220> FEATURE:
<223> OTHER INFORMATION: Artificial sequence obtained through
      biopanning.
```

```
<400> SEQUENCE: 33

Leu Ile Ser Met Gln Ser Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 34

Ile Arg Leu Arg Lys His Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 35

Arg Asn Arg Met Arg Arg Leu
1               5

<210> SEQ ID NO 36
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 36

Arg Arg Ile Pro Leu Gln Leu
1               5

<210> SEQ ID NO 37
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 37

Ile His Arg Met Ile His Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 38

Met Asn Ile Lys Thr Lys Ile
1               5

<210> SEQ ID NO 39
<211> LENGTH: 7
```

```
<212> TYPE: PRT
<213> ORGANISM: Artificial Sequence
<220> FEATURE:
<223> OTHER INFORMATION: Artificial sequence obtained through
      biopanning.

<400> SEQUENCE: 39

Ser Pro Arg Thr Ser Arg Asn
1               5

<210> SEQ ID NO 40
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 40

Gln Ile Thr Leu Arg Ser Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 41

Gln Asn Leu Thr Arg Asn Ile
1               5

<210> SEQ ID NO 42
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 42

Ile Ile Pro Pro Leu Arg Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 43

Asn Leu Pro Met Ser Arg Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 44

Ile Arg Asn Ile Thr Ser His
```

```
<210> SEQ ID NO 45
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 45

Lys Asn Met Pro Arg Ser Met
1               5

<210> SEQ ID NO 46
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 46

Pro Leu Arg Arg Asn Ile Leu
1               5

<210> SEQ ID NO 47
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 47

Leu Gln Thr Asn Pro Ser Met
1               5

<210> SEQ ID NO 48
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 48

Asn Lys Met Pro Arg Ser Met
1               5

<210> SEQ ID NO 49
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 49

Thr Ser Leu Thr Thr Ser Pro
1               5

<210> SEQ ID NO 50
<211> LENGTH: 7
<212> TYPE: PRT
<213> ORGANISM: Artificial Sequence
<220> FEATURE:
<223> OTHER INFORMATION: Artificial sequence obtained through
``` biopanning.

<400> SEQUENCE: 50

Arg Asn Arg Leu Thr Leu Pro
1               5

<210> SEQ ID NO 51
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 51

Lys Ile Pro Thr Leu Ile Asn
1               5

<210> SEQ ID NO 52
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 52

Arg Gly Gln Ser Gln Pro Ser
1               5

<210> SEQ ID NO 53
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 53

Asn Ile Gln Val Gly Gln Pro
1               5

<210> SEQ ID NO 54
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 54

Lys Arg Ser His Leu Ile Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 55

His Gln Ser Arg His Met Ile
1               5

<210> SEQ ID NO 56

```
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 56

Leu Pro Gln Arg Leu Arg Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 57

Ile Leu Arg His Pro His Thr
1               5

<210> SEQ ID NO 58
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 58

Asn Arg Asn Leu Pro Gln Leu
1               5

<210> SEQ ID NO 59
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 59

Ser Gln Arg Arg Thr Arg Ile
1               5

<210> SEQ ID NO 60
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 60

Lys Asn Ile Arg Lys Thr Ile
1               5

<210> SEQ ID NO 61
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 61
```

Thr Thr Arg His Ile Asn Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 62

Ile Arg Met Ser Arg Thr Lys
1               5

<210> SEQ ID NO 63
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 63

Ser Ile Asn Gln Arg Arg Pro
1               5

<210> SEQ ID NO 64
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 64

Thr Ile Arg Lys Lys Asn Leu
1               5

<210> SEQ ID NO 65
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 65

Arg Arg Pro Arg Ile Ser His
1               5

<210> SEQ ID NO 66
<211> LENGTH: 7
<212> TYPE: PRT
<213> ORGANISM: Artificial Sequence
<220> FEATURE:
<223> OTHER INFORMATION: Artificial sequence obtained through
      biopanning.

<400> SEQUENCE: 66

Pro Arg Met Leu Pro Met Ile
1               5

<210> SEQ ID NO 67
<211> LENGTH: 7
<212> TYPE: PRT
<213> ORGANISM: Artificial Sequence
<220> FEATURE:

<223> OTHER INFORMATION: Artificial sequence obtained through
     biopanning.

<400> SEQUENCE: 67

Pro Arg Ile Arg Lys Ser His
1               5

<210> SEQ ID NO 68
<211> LENGTH: 7
<212> TYPE: PRT
<213> ORGANISM: Artificial Sequence
<220> FEATURE:
<223> OTHER INFORMATION: Artificial sequence obtained through
     biopanning.

<400> SEQUENCE: 68

Met His Asn Leu Asn Leu Leu
1               5

<210> SEQ ID NO 69
<211> LENGTH: 7
<212> TYPE: PRT
<213> ORGANISM: Artificial Sequence
<220> FEATURE:
<223> OTHER INFORMATION: Artificial sequence obtained through
     biopanning.

<400> SEQUENCE: 69

Leu Pro Ser Thr Ile His Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Artificial sequence obtained through
     biopanning.

<400> SEQUENCE: 70

Leu Arg Pro Leu Met Asn Arg
1               5

<210> SEQ ID NO 71
<211> LENGTH: 7
<212> TYPE: PRT
<213> ORGANISM: Artificial Sequence
<220> FEATURE:
<223> OTHER INFORMATION: Artificial sequence obtained through
     biopanning.

<400> SEQUENCE: 71

Ile Ile Thr Met Lys Arg Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Artificial sequence obtained through
     biopanning.

<400> SEQUENCE: 72

Arg Lys Lys Ser Arg Ile Arg
1               5

```
<210> SEQ ID NO 73
<211> LENGTH: 35
<212> TYPE: PRT
<213> ORGANISM: Pseudomonas aeruginosa

<400> SEQUENCE: 73

Tyr Gly Ser Thr Glu Arg Leu Pro Phe Tyr Glu Asn Tyr Tyr Ala Gly
1               5                   10                  15

Gly Phe Asn Ser Val Arg Gly Phe Lys Asp Ser Thr Leu Gly Pro Arg
            20                  25                  30

Ser Thr Pro
        35

<210> SEQ ID NO 74
<211> LENGTH: 35
<212> TYPE: PRT
<213> ORGANISM: Pseudomonas stutzeri

<400> SEQUENCE: 74

Tyr Gly Ser Thr Ser Arg Leu Pro Phe Tyr Glu His Tyr Tyr Ala Gly
1               5                   10                  15

Gly Phe Asn Ser Val Arg Gly Phe Glu Asp Ser Ser Leu Gly Pro Arg
            20                  25                  30

Ser Thr Pro
        35

<210> SEQ ID NO 75
<211> LENGTH: 35
<212> TYPE: PRT
<213> ORGANISM: Pseudomonas fluorescens

<400> SEQUENCE: 75

Tyr Gly Ser Thr Asp Gly Leu Pro Phe Tyr Glu Asn Tyr Thr Ala Gly
1               5                   10                  15

Gly Glu Gly Ser Val Arg Gly Phe Glu Ser Gly Thr Leu Gly Pro Pro
            20                  25                  30

Ser Thr Pro
        35

<210> SEQ ID NO 76
<211> LENGTH: 35
<212> TYPE: PRT
<213> ORGANISM: Pseudomonas putida

<400> SEQUENCE: 76

Tyr Gly Ser Thr Asp Gly Leu Pro Phe Tyr Glu Ser Tyr Asn Ala Gly
1               5                   10                  15

Gly Gln Gly Ser Val Arg Gly Phe Lys Asp Gly Thr Leu Gly Pro Pro
            20                  25                  30

Ser Thr Pro
        35

<210> SEQ ID NO 77
<211> LENGTH: 34
<212> TYPE: PRT
<213> ORGANISM: Achromobacter

<400> SEQUENCE: 77

Tyr Gly Ser Lys Asp Tyr Pro Ile Ile Lys Asn Val Tyr Ala Gly Gly
1               5                   10                  15

Ile Gly Thr Val Arg Gly Tyr Glu Gly Ser Ser Leu Gly Pro Arg Asp
```

```
                    20                  25                  30

Ser Lys

<210> SEQ ID NO 78
<211> LENGTH: 34
<212> TYPE: PRT
<213> ORGANISM: Ralstonia

<400> SEQUENCE: 78

Tyr Gly Gly Lys Asp Phe Pro Val Phe Lys Asn Tyr Tyr Ala Gly Gly
1               5                   10                  15

Ile Gly Ser Val Arg Gly Tyr Glu Thr Ser Thr Leu Gly Pro Arg Asp
                20                  25                  30

Ala Asn

<210> SEQ ID NO 79
<211> LENGTH: 34
<212> TYPE: PRT
<213> ORGANISM: Escherichia coli

<400> SEQUENCE: 79

Leu Gly Gly Lys Glu Met Pro Phe Tyr Glu Asn Phe Tyr Ala Gly Gly
1               5                   10                  15

Ser Ser Thr Val Arg Gly Phe Gln Ser Asn Thr Ile Gly Pro Lys Ala
                20                  25                  30

Val Tyr

<210> SEQ ID NO 80
<211> LENGTH: 31
<212> TYPE: PRT
<213> ORGANISM: Acinetobacter
<300> PUBLICATION INFORMATION:
<301> AUTHORS: E. SUGAWARA et al.
<302> TITLE: Alternative folding pathways of hte major porin OprF of
      Pseudomonas aeruginosa
<303> JOURNAL: FEBS Journal
<304> VOLUME: 279
<305> ISSUE: 6
<306> PAGES: 910-918
<307> DATE: 2012-01-12
<300> PUBLICATION INFORMATION:
<301> AUTHORS: E. G. RAWLING et al.
<302> TITLE: Epitope mapping of the Pseudomonas aeruginosa major outer
      membrane porin protein OprF
<303> JOURNAL: Infection and Immunity
<304> VOLUME: 63
<305> ISSUE: 1
<306> PAGES: 38-42
<307> DATE: 1995-01-01

<400> SEQUENCE: 80

Asn Asp Leu Pro Phe Tyr Lys Asn Phe Tyr Ala Gly Gly Tyr Gly Ser
1               5                   10                  15

Val Arg Gly Tyr Asp Asn Ser Ser Leu Gly Pro Lys Tyr Pro Ser
                20                  25                  30
```